(12) United States Patent
Hresko et al.

(10) Patent No.: US 11,364,389 B2
(45) Date of Patent: Jun. 21, 2022

(54) TRAINING MODULES FOR AN EXTERNAL MEDICAL DEVICE

(71) Applicant: ZOLL Medical Corporation, Chelmsford, MA (US)

(72) Inventors: Patrick Hresko, Mount Pleasant, PA (US); Trisha A. Pavel, Pittsburgh, PA (US); Thomas E. Kaib, Irwin, PA (US); Grace Owens, Pittsburgh, PA (US); John Clark, Pittsburgh, PA (US); Rachel H. Carlson, Falls Creek, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 84 days.

(21) Appl. No.: 15/282,323

(22) Filed: Sep. 30, 2016

(65) Prior Publication Data

US 2017/0095674 A1  Apr. 6, 2017

Related U.S. Application Data

(60) Provisional application No. 62/235,883, filed on Oct. 1, 2015.

(51) Int. Cl.
| | |
|---|---|
| *A61N 1/39* | (2006.01) |
| *A61N 1/04* | (2006.01) |
| *G09B 23/28* | (2006.01) |
| *G09B 5/02* | (2006.01) |

(Continued)

(52) U.S. Cl.
CPC ......... *A61N 1/3993* (2013.01); *A61N 1/0484* (2013.01); *A61N 1/3937* (2013.01); *A61N 1/3975* (2013.01); *A61N 1/3987* (2013.01); *G09B 5/02* (2013.01); *G09B 5/04* (2013.01); *G09B 5/06* (2013.01); *G09B 23/28* (2013.01)

(58) Field of Classification Search
CPC .. A61N 1/3925; A61N 1/3987; A61N 1/3993; A61N 1/3702; A61N 1/36514; A61N 1/0456; A61N 1/3956; A61N 1/0484; A61N 1/3937; A61N 1/3975; G09B 5/02; G09B 5/04; G09B 5/06
USPC ........................................................... 607/6
See application file for complete search history.

(56) References Cited

U.S. PATENT DOCUMENTS

| | | |
|---|---|---|
| 4,928,690 A | 5/1990 | Heilman et al. |
| 5,078,134 A | 1/1992 | Heilman et al. |
| 5,741,306 A | 4/1998 | Glegyak et al. |

(Continued)

*Primary Examiner* — Mallika D Fairchild
*Assistant Examiner* — Minh Duc G Pham
(74) *Attorney, Agent, or Firm* — Finch & Maloney PLLC

(57) ABSTRACT

An external medical device is provided which is configured to provide a user with access to one or more training modules. The external medical device includes one or more electrodes configured to detect a cardiac activity of a patient, an audio and/or visual output, and a controller coupled to the audio and/or visual output. The controller is configured to: detect at least one of a predetermined event and a device use pattern; and responsive to detecting the at least one of the predetermined event and the device use pattern, provide the patient access to one or more training modules relating to a use or a configuration of the external medical device via the audio and/or visual output. The device can also include a user interface configured to provide access to at least one training module according to a schedule of training modules for the patient.

25 Claims, 15 Drawing Sheets

(51) Int. Cl.
*G09B 5/04* (2006.01)
*G09B 5/06* (2006.01)

(56) References Cited

U.S. PATENT DOCUMENTS

| | | |
|---|---|---|
| 5,944,669 A | 8/1999 | Kaib |
| 6,065,154 A | 5/2000 | Hulings et al. |
| 6,253,099 B1 | 6/2001 | Oskin et al. |
| 6,280,461 B1 | 8/2001 | Glegyak et al. |
| 6,681,003 B2 | 1/2004 | Linder et al. |
| 8,271,082 B2 | 9/2012 | Donnelly et al. |
| 8,369,944 B2 | 2/2013 | Macho et al. |
| 8,676,313 B2 | 3/2014 | Volpe et al. |
| 8,838,235 B2 | 9/2014 | Cowan et al. |
| 9,067,080 B2 * | 6/2015 | Einy ............... H04M 1/21 |
| 9,079,045 B2 | 7/2015 | Cowan et al. |
| 9,827,435 B2 | 11/2017 | Walker et al. |
| 2003/0004547 A1 * | 1/2003 | Owen .............. A61N 1/046 607/5 |
| 2003/0023277 A1 | 1/2003 | Owen et al. |
| 2007/0219588 A1 * | 9/2007 | Freeman .......... A61N 1/3925 607/5 |
| 2008/0004663 A1 | 1/2008 | Jorgenson |
| 2008/0038706 A1 * | 2/2008 | Dameshek ........ G09B 5/06 434/309 |
| 2009/0035740 A1 * | 2/2009 | Reed .............. G09B 23/288 434/265 |
| 2013/0325096 A1 | 12/2013 | Dupelle et al. |
| 2014/0043149 A1 | 2/2014 | Cowan et al. |
| 2014/0094865 A1 | 4/2014 | Walker et al. |
| 2014/0094866 A1 | 4/2014 | Walker et al. |
| 2015/0039053 A1 | 2/2015 | Kaib et al. |
| 2016/0342761 A1 | 11/2016 | Whiting et al. |
| 2017/0021184 A1 | 1/2017 | Pavel et al. |
| 2017/0296107 A1 | 10/2017 | Reid et al. |

* cited by examiner

Scheduled Training Modules — 574

| Module | Date | Time | Priority |
|---|---|---|---|
| Using the Response Buttons | 09/07/15 | 7:15 AM | 1 |
| Increasing volume | 09/07/15 | 7:00 PM | 3 |
| Garment Cleaning Suggestions | 09/09/15 | 1:00 PM | 3 |
| Calling your Service Representative | 10/01/15 | 7:15 AM | 2 |
| Battery Charging Review | 12/31/15 | 7:15 AM | 1 |

Reschedule — 584

When would you like to view the Battery Charging Training Module?

Date:
- Monday, September 7, 2015
- Tuesday, September 8, 2015
- Wednesday, September 9, 2015
- Thursday, September 10, 2015
- Friday, September 11, 2015

Time:
- 11:00 AM EST
- 11:15 AM EST
- 11:30 AM EST
- 11:45 AM EST

FIG. 10C

TRAINING MODULES FOR AN EXTERNAL MEDICAL DEVICE

CROSS REFERENCE TO RELATED APPLICATION

This application claims priority to U.S. Provisional Patent Application No. 62/235,883 filed Oct. 1, 2015, entitled "Training Modules for an External Medical Device", the disclosure of which is hereby incorporated in its entirety by reference.

TECHNICAL FIELD

The present disclosure relates to an external medical device and, in some aspects, to an external medical device configured to allow a user to access one or more training modules including instructions for using and/or maintaining the device.

BACKGROUND

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

Monitoring devices are also available. For example, such devices operate by monitoring the patient's heart for treatable arrhythmias and, when a treatable arrhythmia is detected, the device applies corrective electrical pulses directly to the heart. Wearable pacing devices and/or defibrillators have been developed for a certain population of patients, e.g., those that may have recently experienced a heart attack, that are susceptible to heart arrhythmias and are at temporary risk of sudden death, or that are awaiting an implantable device.

Typically, a user receives training for operating and maintaining these medical devices when he or she first receives the device from a service representative. The training can include instructions from the service representative in combination with various demonstrations using the device itself. Training is not generally available in the field when the service representative is not available.

SUMMARY

Preferred and non-limiting aspects or embodiments of the present invention will now be described in the following numbered clauses:

Clause 1: An external medical device includes one or more electrodes configured to detect a cardiac activity of a patient; an audio and/or visual output; and a controller coupled to the output. The controller is configured to: detect at least one of a predetermined event and a device use pattern; and responsive to detecting the at least one of the predetermined event and the device use pattern, provide the patient access to at least one training module relating to a use or a configuration of the external medical device via the audio and/or visual output.

Clause 2: The external medical device of clause 1, wherein the at least one training module can include at least one of: a garment laundering training module; a device setup training module; a showering training module; a battery charging training module; an alert training module; an electrode positioning training module; and a training module providing instructions for connecting the one or more electrodes to the controller.

Clause 3: The external medical device of clause 1 or clause 2, wherein the controller can be configured to provide the patient access to the at least one training module by providing a notification to the patient to self-administer the at least one training module via the output.

Clause 4: The external medical device of any of clauses 1 to 3, wherein the device can further include one or more sensors for detecting a status of the external medical device. The controller can be configured to detect misuse of the external medical device based, at least in part, on measurements received from the one or more sensors and to inform the patient of the misuse via the output.

Clause 5: The external medical device of clause 4, wherein informing the patient of the misuse can include providing a notification to the patient to self-administer at least one training module associated with proper use of the external medical device.

Clause 6: The external medical device of clause 4 or clause 5, wherein the one or more sensors for detecting a status of the external medical device can include one or more of an accelerometer, a temperature sensor, a gyroscope sensor, a drop detection sensor, a battery charge sensor, and a battery viable life sensor.

Clause 7: The external medical device of any of clauses 1 to 6, wherein the device can further include one or more sensors for determining a configuration of the external medical device.

Clause 8: The external medical device of clause 7, wherein the controller can be configured to identify an improper configuration of the external medical device based, at least in part, on information received from the one or more sensors and to inform the patient of the improper configuration via the output.

Clause 9: The external medical device of clause 8, wherein informing the patient of the improper configuration can include providing a notification to the patient to self-administer at least one training module associated with proper configuration of the external medical device.

Clause 10: The external medical device of any of clauses 1 to 9, wherein the device can further include a transceiver configured to receive the at least one training module or an updated training module from an external source.

Clause 11: The external medical device of clause 10, wherein the controller can be configured to provide a notification to a third party via the transceiver upon detection of at least one of the predetermined event and the device use pattern.

Clause 12: The external medical device of any of clauses 1 to 11, wherein the at least one training module can include one or more of a video, an animation sequence, a plurality of still images, text messages, recorded messages, interactive content, quizzes, and surveys.

Clause 13: The external medical device of any of clauses 1 to 13, wherein providing the patient access to at least one training module can include scheduling a time for the patient to use the training module, informing the patient of the scheduled time via the output, and, subsequently, providing notifications to the patient to remind the patient of the scheduled viewing time.

Clause 14: The external medical device of clause 13, wherein the controller can be configured to provide a notification to the patient prior to beginning a scheduled training module. The notification can include an option for delaying the training module to a later time.

Clause 15: The external medical device of any of clauses 1 to 14, wherein the device can further include one or more sensors configured to measure information representative of one or more of the following: a respiration level of the patient, a heart sound and movement of the patient, a lung sound and movement of the patient, a tissue fluid level of the patient, a blood pressure of the patient, a glucose level of the patient, and a blood oxygenation level of the patient.

Clause 16: The external medical device of any of clauses 1 to 15, wherein the device can comprise at least one of a cardiac monitor, a defibrillator, and a wearable defibrillator.

Clause 17: The external medical device of any of clauses 1 to 16, wherein the device can comprise a wearable external medical device.

Clause 18: The external medical device of clause 17, wherein the wearable external medical device can include a garment worn by the patient.

Clause 19: The external medical device of clause 17 or clause 18, wherein the wearable external medical device can include adhesive patches including at least one of sensing electrodes and therapy electrodes.

Clause 20: The external medical device of any of clauses 17 to 19, wherein the one or more electrodes can be configured to collect data representative of the cardiac activity of the patient over a period of time during which the patient is using the wearable medical device.

Clause 21: The external medical device of clause 20, wherein the data collected over the period of time can be continuously or substantially continuously collected during the period of time.

Clause 22: An external medical device for providing a patient access to at least one training module includes: a plurality of sensors for monitoring a physiological parameter of a patient; and a controller including a user interface. The user interface can be configured to provide access to the at least one training module relating to a use or a configuration of the external medical device according to a schedule of training modules for the patient.

Clause 23: The external medical device of clause 22, wherein, prior to initial use of the external medical device, the schedule of training modules for the patient includes at least a follow-up device setup training module.

Clause 24: The external medical device of clause 22 or clause 23, wherein the follow-up device setup training module can be scheduled for viewing between 24 and 72 hours after the initial use of the external medical device.

Clause 25: The external medical device of any of clauses 22 to 14, wherein the schedule of training modules includes one or more reoccurring training modules that are scheduled for repeated use by the patient at predetermined intervals.

Clause 26: The external medical device of any of clauses 22 to 25, wherein the user interface can be configured to provide a notification to the patient about a time for using the at least one training module.

Clause 27: The external medical device of clause 26, wherein providing the notification to the patient about the time for using the at least one training module can include providing the patient an option to delay use of the at least one training module for a predetermined period of time.

Clause 28: The external medical device of clause 27, wherein the user interface can be configured to monitor a number of times that use of the at least one training module is delayed by the patient and to provide a different notification to the patient about the time for using the at least one training module as the number of times that use is delayed increases.

Clause 29: The external medical device of any of clauses 22 to 28, wherein the controller can include computer readable memory, and the at least one training module can be stored on the computer readable memory.

Clause 30: The external medical device of any of clauses 22 to 29, wherein the device can further include a transceiver. The at least one training module can be received from an external source via the transceiver.

Clause 31: The external medical device of any of clauses 22 to 30, wherein the plurality of sensors can be configured to measure information representative of one or more of the following: a respiration level of the patient, a heart sound and movement of the patient, a lung sound and movement of the patient, a tissue fluid level of the patient, a blood pressure of the patient, a glucose level of the patient, and a blood oxygenation level of the patient.

Clause 32: The external medical device of any of clauses 22 to 31, wherein the device further includes at least one of a cardiac monitor, a defibrillator, and a wearable defibrillator.

Clause 33: The external medical device of any of clauses 22 to 32, wherein the device can comprise a wearable external medical device.

Clause 34: The external medical device of clause 33, wherein the wearable external medical device can include a garment worn by the patient.

Clause 35: The external medical device of clause 33 or clause 34, wherein the wearable external medical device can include adhesive patches including at least one of sensing electrodes and therapy electrodes.

Clause 36: An external medical device includes: one or more sensors configured to detect at least one of a physiological parameter of a patient and a status of the external medical device; an audio and/or visual output; and a controller coupled to the audio and/or visual output. The controller can be configured to process signals received from the one or more sensors to identify changes in one or more of patient condition and device function; and responsive to the identification of changes in one or more of patient condition and device function, provide the patient access to at least one training module selected based on the one or more changes.

Clause 37: The external medical device of clause 36, wherein the changes can include one or more of: a degradation in patient health; a degradation in patient compliance with device operating instructions; a degradation in signal quality received from the one or more sensors; an increase in a number of alarms issued by the device, an increase in movement of the device; an increase in a number of times that the patient removes or disconnects the external medical device; a degradation in device function; and a degradation in an average power level of a device battery.

Clause 38: The external medical device of clause 36 or clause 37, wherein the controller can be configured to identify an effectiveness of a service representative for the patient based, at least in part, on changes identified in one or more of patient condition and device function.

Clause 39: A wearable defibrillator includes: a garment configured to be worn by a patient; at least one therapy pad connected to or embedded in the garment and connected to a defibrillation shock generator; one or more electrodes configured to detect cardiac activity of a patient; one or more sensors configured to monitor a status of the defibrillator; and a controller operatively connected with the defibrillation shock generator, one or more electrodes, and one or more sensors. The controller can be configured to detect at least one of a predetermined event and a device use pattern based, at least in part, on information from the one or more sensors and, responsive to detecting the at least one of the predetermined event and the device use pattern, provide the patient access to at least one training module relating to a use or a configuration of the wearable defibrillator via an output device in communication with the controller.

Clause 40: The wearable defibrillator of clause 39, wherein the one or more sensors can include one or more of a contact sensor to confirm contact between the one or more electrodes and the patient; a sensor associated with a latch or buckle of the garment to identify if the garment is secured to the patient; a sensor for confirming that the electrodes are connected to the controller; a sensor for identifying a position of the electrodes on the patient's body; and a sensor associated with the therapy pads to determine a position of the therapy pad relative to the patient.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

FIG. 10A is an example screen including a list of scheduled training modules on an external medical device;

FIGS. 10B and 10C are example screens for delaying and rescheduling training modules on an external medical device.

DETAILED DESCRIPTION

Figure 1:
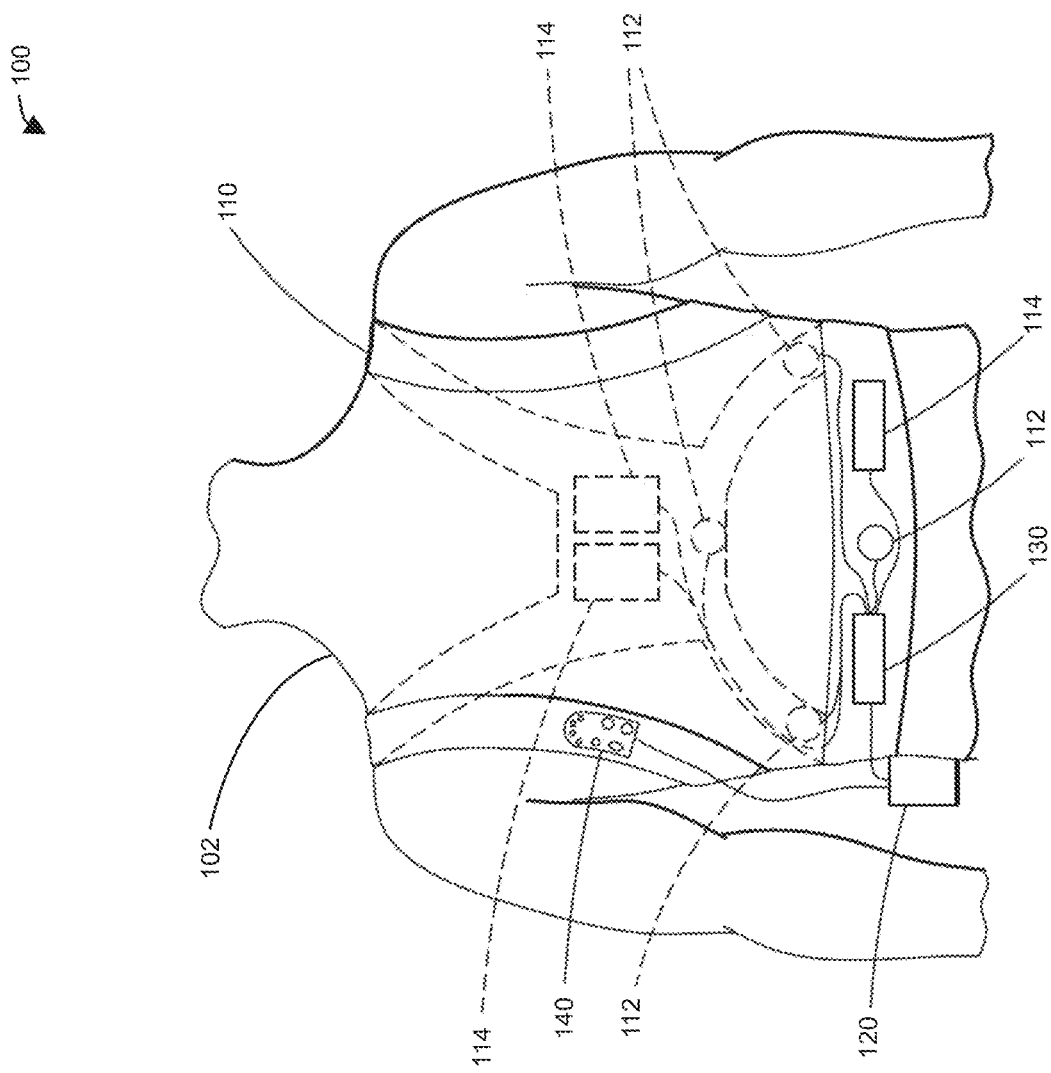
FIG. 1 is a schematic drawing of a wearable medical device.

As used herein, the singular form of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Aspects of the present disclosure are directed to monitoring and/or therapeutic medical devices that allow a user (e.g., a patient) to access training demonstrations, video and audio lessons, and/or text instructions (referred to collectively as "training modules") for operating and maintaining an external medical device while the device is in use in the field (e.g., when a service representative or medical professional is not available). For example, the ability to access training modules while the medical device is in use may help patients who do not retain or remember instructions received from service representatives or medical professionals when they first receive the device. In particular, through interviews with patients using ambulatory medical devices, it has been determined that users either have difficulty remembering instructions given during device setup and/or cannot recognize how some of the instructions may be applied in particular scenarios which may arise while using the device.

In some implementations, the patient may continue to be protected by the medical device (e.g., monitored for a medical condition and/or treated if necessary) during the administration of the one or more training modules.

In order to address issues of user information recall and to improve user compliance with instructions, the external medical devices described herein can be configured to provide one or more training modules to the user. The training modules include information and instructions to assist the user in device operation and maintenance, and can include, for example, animations, written content, video displays, sequences of slides, and audio content. The user is permitted to access the training modules while the device is in the field (e.g., being used to monitor an ambulatory patient, and in situations in which a medical professional or device service representative is not present). Further, the user can access the training modules while the device is actively monitoring the user and/or as the device is actively determining whether to provide therapy to the user. The training modules can supplement and/or reinforce training provided to the user by service representative.

As noted, such training modules may be directed to patients who are not in a medically-supervised environment. Accordingly, the training modules can be based on improving patient retention of information based on principles of readiness, exercise, and effect. In some implementations, training modules may be configured to take advantage of learning opportunities and times when patients are ready to learn (e.g., when the patient is in the comfort of his or her home and prepared to be trained on the device). The training modules can be configured to repeat information, provide exercises and/or quizzes to test retention of the information, and allow for patients to practice the information they have learned through simulations and/or drills. Further, the training modules can be configured to be delivered in a manner that maximizes information retention (e.g., be pleasing and interesting, use mnemonics, etc.). For instance, the training modules may be implemented through a mix of graphics, animation, and audible instructions configured to hold the interest and attention of the patient. In one implementation, the training modules can be configured to use effective learning principles, such as extensive graphics, animation(s), cartoons, humor elements, and other such modes of delivering the information.

In some examples, the training modules may include previously created or recorded modules. For example, such previously created or recorded modules can include modules that users may view again to refresh their knowledge and training with respect to particular topics. Alternatively or in addition, the training modules can be new or newly updated training modules, which were not available when the user first received the external medical device. The training modules can be stored locally on the device or accessible or downloadable to the device from a remote site, such as a remote computer server. For example, a training module can include videos, images, text, animations, and/or other multimedia content that may be "streamed" on the device from a remote server.

While the training modules described herein are generally targeted for the user of the device, it is appreciated that the information in training modules can be of interest to other individuals, such as family members or caregivers. The family members or caregivers generally interact with the user on a regular basis and, in some cases, can be at least partially responsible for operating and maintaining the external medical device. For example, in some scenarios, a user can view or use an initial or device setup training module when he or she first receives the device from the service representative. At a later time, the user can view the training module a second time with family members or caregivers so that multiple individuals will know how to respond if, for example, the device emits an alert or administers treatment to the patient.

In some examples, the external medical device can include one or more sensors configured to detect cardiac activity of a patient and a controller comprising an audio and/or visual output or output component. Based on signals received from the cardiac activity sensors and/or additional sensors connected to or associated with the device, the controller can be configured to detect a predetermined event or use pattern and, responsive to detection of the event or use pattern, provide the patient access to at least one training module related to the identified event or use pattern. In this way, the external medical device can automatically select one or more training modules that the user would benefit from viewing or using. For example, predetermined events can include, among others, device impact detection or excessive force applied to one or more components of the device, excessive humidity, excessive water exposure, misuse of the device, improper configuration, noncompliance with prescribed and/or recommended use, etc. For example, sensors can be configured to monitor configuration of the device (e.g., electrode position, electrode signal quality, device status, battery charge level, garment status) and identify sensor readings that the device is improperly configured or being misused. Once a particular example of device improper configuration and/or misuse is identified, a training module directed to the identified issue can be provided to the user or scheduled for use by the user at a later time and date. A predetermined event may also be a physiological event (e.g., identification of an arrhythmia) by the wearable device. In other examples, a predetermined event may be related to a device action or status, such as providing treatment to the patient.

In some examples, the medical device can be configured to issue or provide reminders (e.g., electronic notifications) to the user and/or caregiver reminding him or her that a training module may be accessed and viewed. The medical device can provide reminders until the appropriate training has been completed. In some examples, notifications can increase if the user has avoided or ignored previously provided reminders and/or fails to complete the training module within a reasonable period of time. For example, a frequency or conspicuousness of reminders can increase until the notification or reminder is complied with and the user access or views the training module. For example, increasing a conspicuousness of reminders can include making successive reminder notifications larger and more apparent (e.g., using larger fonts, brighter colors, changing contrast, accompanying visual notifications with audible and/or tactile alerts, increasing audible and/or tactile alert intensity, etc.)

In some examples, the medical device can include communications circuitry for receiving updated or new training modules from an external source. Training modules can be received automatically, such as by batch download when updated modules are available. The user can also select specific modules that he or she would like to view. If the selected modules are not stored locally on the external medical device, the selected training module can be downloaded from a remote source. Training modules can also be selected for and provided to the user or patient by a service representative. For example, if the representative identifies that certain training modules would be helpful for a particular user, the representative can send the selected training module to the user's device. In some examples, the medical device can include a user interface or scheduling function for manually or automatically selecting when a training module can be viewed by the user. The medical device can be configured to provide alerts or notifications reminding the user to access and view the training module at the scheduled time.

In some examples, during or following a training module, the user can initiate communication with the service representative to discuss the information covered and/or to suggested or request changes to the device settings based on topics covered in the training module. For example, an audio and/or video communication link between the user and representative may comprise a real-time telephone call, a real-time video call (e.g., a Skype® call, a FaceTime® call, or other video conferencing call), a Push-to-Talk (PTT) connection, or other communication link capable of communicating audio and/or video data between the user and the service representative.

Example External Medical Devices:

More generally, this disclosure relates to components, modules, subsystems, circuitry and/or techniques for use in external medical devices. For example, such components, modules, subsystems, circuitry and/or techniques can be used in the context of medical devices for providing treatment to and/or monitoring a patient. For example, such medical devices can include monitoring devices configured to monitor a patient for certain conditions. In some implementations, such devices are capable of, in addition to monitoring for patient conditions, providing treatment to a patient based on detecting a predetermined patient condition.

In some implementations, the medical device as described herein is an external or non-invasive medical device (e.g., in contrast to internal or invasive devices, such as implantable medical devices). For example, the external medical device can be a cardiac monitoring and/or automated pacing device or defibrillator, such as an in-facility continuous monitoring defibrillator (e.g., for patients that are confined to a limited space within a facility, such as, within a hospital environment, to a patient's room) or outpatient wearable defibrillators.

In some implementations, an external medical device can be an automated cardiac monitor or defibrillator that can be used in certain specialized conditions and/or environments such as in combat zones or within emergency vehicles. The medical device can be configured so that it can be used immediately (or substantially immediately) in a life-saving emergency. For example, the external medical device can be an automated external defibrillator (AED). Such AEDs are available from ZOLL® Medical Corporation of Chelmsford, Mass.

In some implementations, the external medical device is an ambulatory device (e.g., a device that is capable of and designed for moving with the patient as the patient goes about his or her daily routine). In some examples, the external medical device can be configured as a wearable defibrillator, such as the LifeVest® wearable defibrillator available from ZOLL® Medical Corporation of Chelmsford, Mass.

The devices as described herein may be capable of continuously, substantially continuously, long-term and/or extended use or wear by, or attachment or connection to a patient.

For example, devices as described herein may be capable of being used or worn by, or attached or connected to a patient, without substantial interruption for a predetermined period of time. In some examples, such devices may be capable of being used or worn by, or attached or connected to a patient for example, up to hours or beyond (e.g., weeks, months, or even years).

In some implementations, such devices can be removed for a period of time before use, wear, attachment, or connection to the patient is resumed, e.g., to change batteries, to change or wash the garment, and/or to take a shower, without departing from the scope of the examples described herein.

The devices as described herein may be capable of continuously, substantially continuously, long-term and/or extended monitoring of a patient.

For example, devices as described herein may be capable of providing cardiac monitoring without substantial interruption for a predetermined period of time. In some examples, such devices may be capable of continuously or substantially continuously monitoring a patient for cardiac-related information (e.g., ECG information, including arrhythmia information, heart sounds, etc.) and/or non-cardiac information (e.g., blood oxygen, the patient's temperature, glucose levels, and/or lung sounds), for example, up to hours or beyond (e.g., weeks, months, or even years).

In some implementations, such devices may be powered down for a period of time before monitoring is resumed, e.g., to change batteries, to change or replace the garment, and/or to take a shower, without departing from the scope of the examples described herein.

In some instances, the devices can carry out its monitoring in periodic or aperiodic time intervals or times. For example, the monitoring during intervals or times can be triggered by a user action or another event. For example, one or more durations between the periodic or aperiodic intervals or times can be user-configurable.

In various implementations, the devices may be operated on battery power for a duration of the device's use after which the batteries may be replaced and/or recharged.

In some implementations, the medical device as described herein can be a hospital based medical device including, for example, a cardiac monitoring device, a defibrillator and/or pacing device. For example, such a hospital based device can include a defibrillator and/or pacing device configured for continuous or substantially continuous use, wear, connection, attachment, or monitoring to/of a patient in a hospital environment. The hospital based device can include a plurality of therapy and sensing electrodes that are attached to the patient's skin. In some examples, the sensing and/or therapy electrodes are disposable adhesive electrodes. In some implementations, the electrodes are affixed to an electrode assembly (a patch), which can then be adhesively attached to the patient's skin. The sensing and/or therapy electrodes can be attached to the patient's skin at particular locations as prescribed by a trained professional.

In some implementations, the medical device as described herein can be configured to monitor a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, the short-term outpatient defibrillator can include a plurality of electrodes and/or an electrode assembly (patch) that can be adhesively attached to the patient's skin. The patient may replace the electrodes and/or patches as prescribed.

For example, the medical device can include a user interface component for interacting with the medical device. For example, the user interface component can include at least one caregiver interface and at least one patient interface. The device can include one or more input mechanisms (e.g., buttons) that are available via the patient interface so that the patient can interact with the device to respond to a treatment alert. In some examples, the medical device issues a treatment alert before providing a treatment shock, and if the patient does not respond to the treatment alert (e.g., by holding down one or more response buttons), the device can deliver the treatment shock to restore normal heart rhythm.

Other example external devices capable of interacting with the information displaying systems and methods disclosed herein and/or techniques described herein include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the automated defibrillators described herein can be pacing-enabled, e.g., capable of providing therapeutic pacing pulses to the patient. In an example, the external medical devices as described herein can be ambulatory, e.g., the device is capable of and designed for moving with the patient.

Example Therapeutic Medical Device:

With reference to FIG. 1, an example wearable medical device 100, such as a wearable defibrillator, is illustrated. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944; the disclosure of each of which is incorporated herein by reference in its entirety. The wearable medical device 100 includes a plurality of sensing electrodes 112 that can be disposed at various positions about the user's body. The sensing electrodes 112 are electrically coupled to a medical device controller 120 through a connection pod 130. In some implementations, some of the components of the wearable medical device 100 are affixed to a garment 110 that can be worn on the patient's torso. For example, as shown in FIG. 1, the controller 120 can be mounted on a belt worn by the patient. The sensing electrodes 112 and connection pod 130 can be assembled or integrated into the garment 110 as shown. The sensing electrodes 112 are configured to monitor the cardiac function of the patient (e.g., by monitoring one or more cardiac signals of the patient). While FIG. 1 shows four sensing electrodes 112, additional sensing electrodes may be provided, and the plurality of sensing electrodes 112 may be disposed at various locations about the patient's body.

The wearable medical device 100 can also optionally include a plurality of therapy electrodes 114 that are electrically coupled to the medical device controller 120 through the connection pod 130. The therapy electrodes 114 are configured to deliver one or more therapeutic defibrillating shocks, pacing pulses, and/or TENS pulses to the body of the user if it is determined that such treatment is warranted. The connection pod 130 may include electronic circuitry and one or more sensors (e.g., a motion sensor, an accelerometer, etc.) that are configured to monitor patient activity. In some implementations, the wearable medical device 100 may be a monitoring only device that omits the therapy delivery capabilities and associated components (e.g., the therapy electrodes 114). In some implementations, various treatment components may be packaged into various modules that can be attached or removed from the wearable medical device 100 as needed.

As shown in FIG. 1, the wearable medical device 100 may include a user interface pod 140 that is electrically coupled to, integrated in, and/or integrated with, the user interface of the medical device controller 120. The user interface pod 140 can be attached to the patient's clothing or to the garment 110, for example, via a clip (not shown) that is attached to a portion of the user interface pod 140. Alternatively, the user interface pod 140 may simply be held in a person's hand. For example, such a user interface pod 140 can be a smartwatch or a smartphone. In some examples, the user interface pod 140 may communicate wirelessly with the user interface of the medical device controller 120, for example, using a Bluetooth®, Wireless USB, ZigBee, Wireless Ethernet, GSM, or other type of communication interface.

The controller 120 can include response buttons and a touch screen that the patient can interact with in order to communicate with the medical device 100. The controller 120 also includes a speaker for communicating information to the patient and/or a bystander. In some examples, when the controller 120 determines that the patient is experiencing cardiac arrhythmia, the speaker can issue an audible alarm to alert the patient and bystanders to the patient's medical condition. In some examples, the controller 120 can instruct the patient to press and hold one or both of the response buttons on the medical device controller 120 to indicate that the patient is conscious, thereby instructing the medical device controller 120 to withhold the delivery of one or more therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient.

Figure 2B:
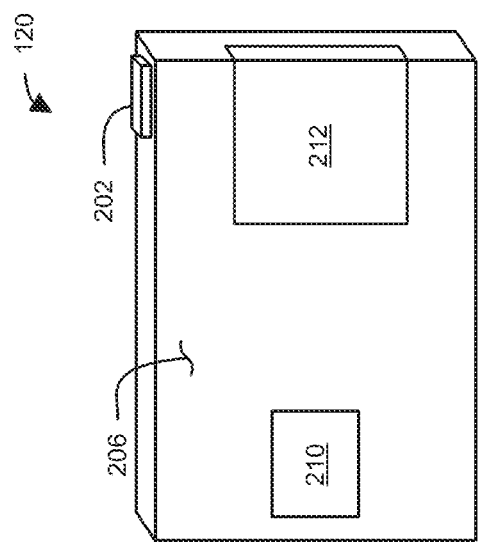
FIG. 2B is a block diagram of a rear view of the example monitor of FIG. 2A.
Figure 2A:
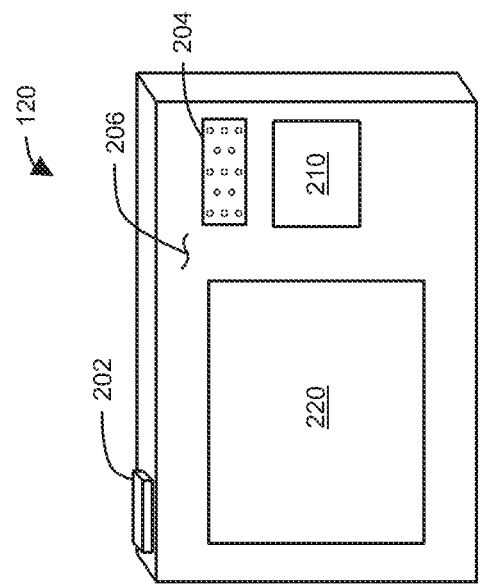
FIG. 2A is a block diagram of a front view of an example monitor for a wearable medical device.

With reference to FIGS. 2A and 2B, an example of the medical device controller 120 is illustrated. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The controller 120 includes a user interface such as a touch screen 220 that can provide information to the patient, caregiver, and/or bystanders. The patient and/or caregiver can interact with the touch screen 220 to control the medical device 100. The controller 120 also includes a speaker 204 for communicating information to the patient, caregiver, and/or the bystander. The controller 120 includes one or more response buttons 210. In some examples, when the controller 120 determines that the patient is experiencing cardiac arrhythmia, the speaker 204 can issue an audible alarm to alert the patient and bystanders to the patient's medical condition. In some examples, the controller 120 can instruct the patient to press and hold one or both of the response buttons 210 to indicate that the patient is conscious, thereby instructing the medical device controller 120 to withhold the delivery of therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient. The medical device controller 120 may further include a port 202 to removeably connect sensing devices (e.g., ECG sensing electrodes 112) and/or therapeutic devices (e.g., therapy electrodes 114 shown in FIG. 1) to the medical device controller 120.

Figure 3:
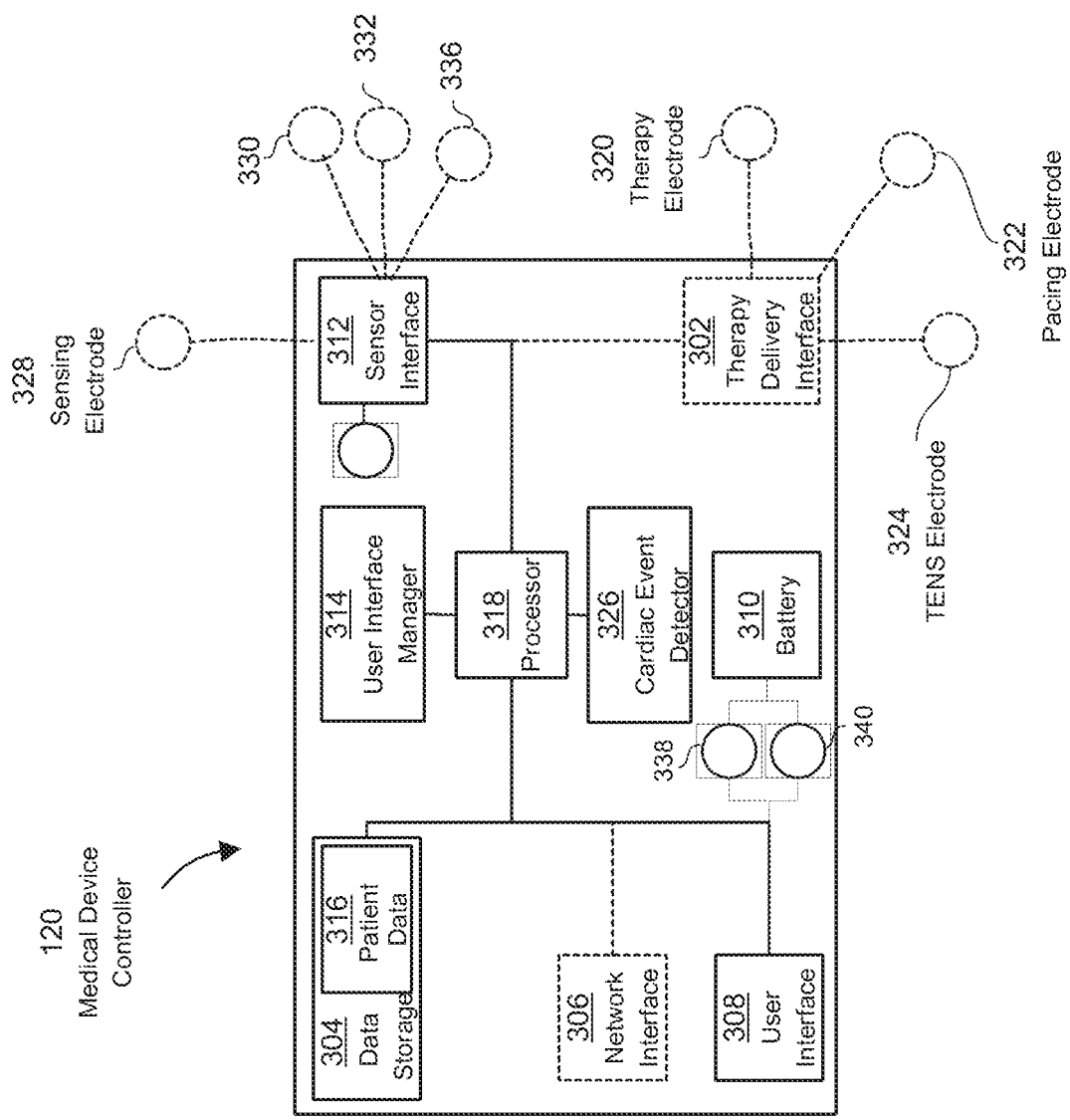
FIG. 3 is an example schematic diagram of a wearable medical device.

With reference to FIG. 3, a schematic example of the medical device controller 120 of FIGS. 1, 2A, and 2B is illustrated. As shown in FIG. 3, the controller 120 includes at least one processor 318, a user interface manager 314, a sensor interface 312, an optional therapy delivery interface 302, data storage 304 (which may include patient data storage 316), an optional network interface 306, a user interface 308 (e.g., including the touch screen 220 shown in FIGS. 2A and 2B), and a battery 310. The sensor interface 312 can be coupled to any one or combination of sensors to receive information indicative of cardiac activity. For example, the sensor interface 312 can be coupled to one or more sensing devices including, for example, sensing electrodes 328, contact sensors 330, pressure sensors 332, and accelerometers or motion sensors 334. The therapy delivery interface 302 (if included) may be coupled to one or more electrodes that provide therapy to the patient including, for example, one or more therapy electrodes 320, pacing electrodes 322, and/or TENS electrodes 324. The sensor interface 312 and the therapy delivery interface 302 may implement a variety of coupling and communication techniques for facilitating the exchange of data between the sensors and/or therapy delivery devices and the controller 120.

In some examples, the network interface 306 can facilitate the communication of information between the controller 120 and one or more other devices or entities over a communications network. For example, the network interface 306 may be configured to communicate with a server (e.g., a remote server) where a caregiver can access information related to the patient. As discussed in more detail below with reference to FIG. 4, the network interface 306 may facilitate communication between the medical device controller 120 and a base station associated (e.g., paired) with the medical device controller.

In some examples, the medical device controller includes a cardiac event detector 326 to monitor the cardiac activity of the patient and identify cardiac events experienced by the patient based on received cardiac signals. In other examples, cardiac event detection can be performed using algorithms for analyzing patient ECG signals obtained from the sensing electrodes 328. Additionally, the cardiac event detector 326 can access patient templates (e.g., which may be stored in the data storage 304 as patient data 316) that can assist the cardiac event detector 326 in identifying cardiac events experienced by the particular patient (e.g., by performing template matching algorithms).

The at least one processor 318 can perform a series of instructions that control the operation of the other components of the controller 120. In some examples, the user interface manager 314 is implemented as a software component that is stored in the data storage 304 and executed by the at least one processor 318 to control, for example, the user interface component 308. The user interface manager 314 can control various outputs or output components and/or devices of the medical device controller 300 to communicate with external entities consist with various acts and/or display screens described herein. For example, such outputs or output components and/or devices can include speakers, tactile and/or vibration output elements, visual indicators, monitors, displays, LCD screens, LEDs, Braille output elements, and the like.

In some implementations, the user interface 308 can include one or more interfaces for communicating and/or interacting with different external entities. For example, such interfaces can include a caregiver interface for communicating and/or interacting with a caregiver (e.g., a nurse, a physician, a physician's aide, or other such individual or entity), a patient interface for a patient, a patient service representative interface for a patient service representative, or a service interface for a service technician, among others. For example, the one or more interfaces can be displayed on a same physical display and/or touchscreen. In some cases, the external entities may be assigned separate security credentials that may be provided before access is granted to the corresponding interface. In some examples, the one or more interfaces can be displayed on different physical displays and/or touchscreens. For example, a caregiver interface may be displayed on a first display, and a patient interface may be displayed on a second, different display.

For example, the user interface manager 314 may cause the user interface 308 to switch from a first one of the one or more interfaces to a second one of the one or more interfaces depending on a current device function or operation. As an example, the user interface 308 can display "Call Caregiver" to the patient via a patient interface when a device related event is detected. When the caregiver arrives, he or she may provide his or her security credentials and access a caregiver interface for addressing the device related event.

Example Monitoring Medical Device:

In some examples, the medical device can be a patient monitoring device, which can be configured to monitor one or more of a patient's physiological parameters without an accompanying treatment component. For example, a patient monitor may include a cardiac monitor for monitoring a patient's cardiac information. Such cardiac information can include, without limitation, heart rate, ECG data, heart sounds data from an acoustic sensor, and other cardiac data. In addition to cardiac monitoring, the patient monitor may perform monitoring of other relevant patient parameters, including glucose levels, blood oxygen levels, lung fluids, lung sounds, and blood pressure.

An example cardiac monitoring medical device (e.g., a cardiac monitor) may be similar to wearable medical device 100 described with reference to FIGS. 1-3 and omit, for example, the therapy electrodes 114 and/or the therapy delivery interface 302. In some implementations, the cardiac monitor is capable of and designed to be worn by a patient who is at risk of developing cardiac problems, but who does not yet meet criteria to be outfitted with a medical device that includes a treatment component (e.g., a defibrillator). Thus, the cardiac monitor can be prescribed so that continuous and/or event-based data can be sent from the cardiac monitor to a remote server. A caregiver can access the data from the remote server and determine whether the patient is experiencing or has experienced a cardiac problem. In some implementations, after determining that the patient is experiencing a cardiac problem, the caregiver can instruct the patient to begin wearing a medical device with treatment capabilities.

In some implementations, the patient can interact with the user interface 308 to identify a patient symptom. The user interface 308 can include a drop down menu or check list that allows the patient to select a particular symptom from a list of alternatives. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac event detector 326 can cause a portion of patient physiological information (e.g., in the form of a cardiac signal) to be captured for a length of time that is based on when the symptom was experienced. For example, the cardiac event detector 326 can cause a portion of an ECG signal of the patient to be captured. The portion of the ECG signal is sometimes referred to herein as an ECG strip. In some implementations, the cardiac monitor can continuously record ECG data, and at the same time also identify and record one or more ECG strips relating to one or more events of interest (e.g., patient-reported symptoms, events detected by the cardiac event detector 326, etc.). As such, if a caregiver wishes to view ECG data for a period of time prior to or after the recorded ECG strip relating to an event of interest, such data is available for review from the continuously-recorded ECG data.

Figure 4:
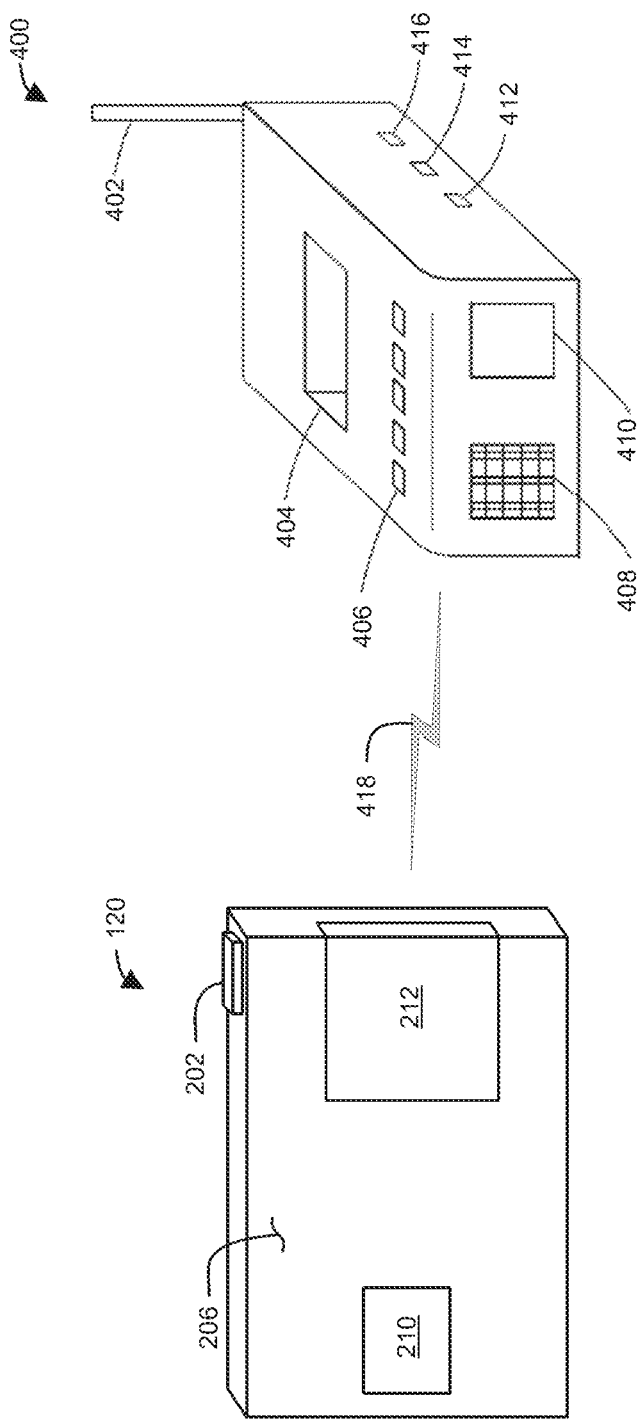
FIG. 4 is an example block diagram illustrating functional components of a patient monitor (e.g., a cardiac monitor)

Example Base Station for an External Medical Device:

In some examples, the medical device controller may be in communication with a base station capable of performing a number of different functions. With reference to FIG. 4, an example medical device controller 120 in communication with a base station 400 is illustrated. As illustrated, the base station 400 includes an antenna 402, a battery charging bay 404, one or more buttons 406, a speaker 408, a display 410, and one or more communication interfaces 412, 414, and 416. It is appreciated that the base station 400, in some examples, may omit one or more of the elements depicted in FIG. 4.

The base station 400 communicates with the medical device controller via, for example, wired or wireless communication link 418. With respect to wireless communication, such a link 418 may be implemented through any one or combination of wireless communication standards and protocols including, for example, BLUETOOTH®, Wireless USB, ZigBee, and Wireless Ethernet. In some examples, the medical device controller 120 may be paired to (e.g., connected to) a particular base station 400 through one or more procedures as described further below. The medical device controller 120 may provide, for example, information regarding the patient's medical condition and/or the status of the medical device to the base station 400.

The information received by the base station 400 may be communicated over a wired or wireless network shortly after it is received by the base station 400, or alternatively, may be stored in a memory of the base station 400 and communicated over the network at a later time. For example, the network can be a telephone or cellular service network (e.g., Global System for Mobile Communications (GSM), High Speed Packet Access, mobile network standards known as 3G, 4G, Long Term Evolution (LTE), or LTE Advanced, or the like. For example, the network can be a wired computer network that connects the base station 400 to a local area network (LAN), wide area network (WAN), the Internet, or the like. To facilitate wired network connections, the base station 400 can include one or more ports (e.g., RJ-45, or telephone cable ports) as further described below. The information that is communicated by the base station 400 may be retained in the memory of the base station 400.

Another of the functions performed by the base station 400 is to store and/or communicate information received from the medical device controller 120 over the wired or wireless communication network. For example, information relating to the device and/or patient's medical condition over a period of time may be communicated periodically or aperiodically by the base station 400 to a remote location. For example, the remote location can include equipment for securely receiving such medical data over the network. For example, the remote location may be a technical service center for receiving and processing the information from the base station 400. In some examples, the information may be complied into a report and provided to a medical care provider, e.g., the patient's doctor in a report. Such reports may be configured to be provided periodically, such as daily, weekly, or monthly, or in response to a user, device, or doctor triggered event.

For example, the remote location may be a medical service provider, such as a doctor, so that the doctor may remotely monitor the patient's medical condition. The base station 400 also includes several different communication interfaces including: a device communication interface 412 to receive information from the controller 120 of the medical device controller 120, a telephone network interface 414 to communicate, via a telephone network, the information received from the medical device controller 120, and a network interface 416 to communicate, via a wired network connection, the information received from the medical device controller 120. In certain embodiments, the base station 400 also includes an antenna 402 that can wirelessly communicate the information received from the medical device controller 120 via a cellular (e.g., 2G, 3G, and 4G) network.

In some examples, the base station 400 is capable of charging a rechargeable battery for the medical device controller 120. In these examples, the base station 400 may include a battery charging bay 404 constructed to receive and charge a battery for the medical device controller (e.g., battery 212). The medical device may be provided with multiple batteries to enable a patient and/or caregiver to charge one battery while another charged battery is used to provide power to the medical device. The batteries may be swapped between the medical device controller 120 and the base station 400 once the battery in the medical device controller is depleted (or near depleted). It is appreciated that the base station 400 may include any number of battery charging bays 404 to, for example, charge multiple batteries for the medical device controller 120 simultaneously.

Figure 5:
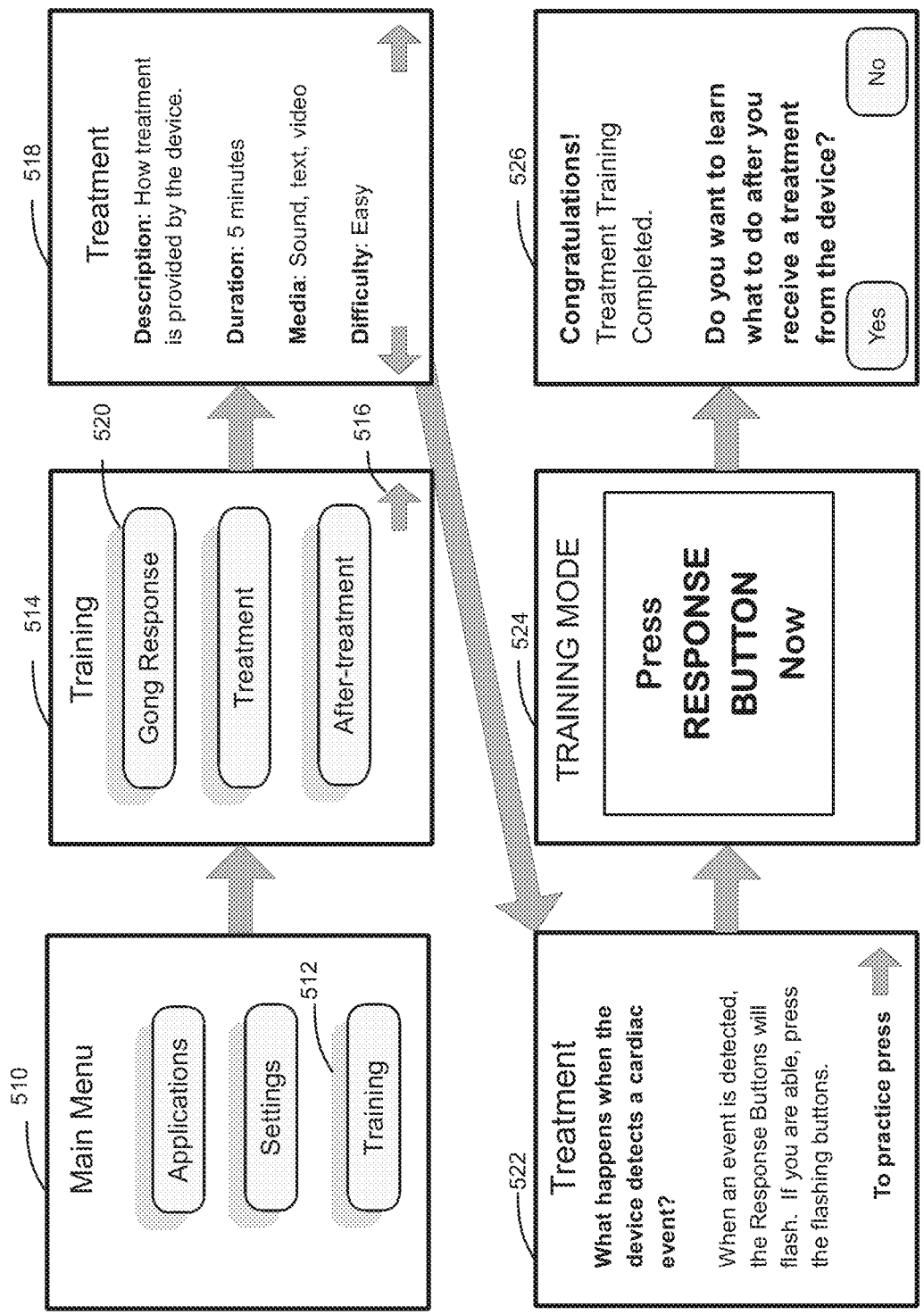
FIG. 5 is an example set of screens for selecting and accessing a training module on an external medical device.
Figure 6:
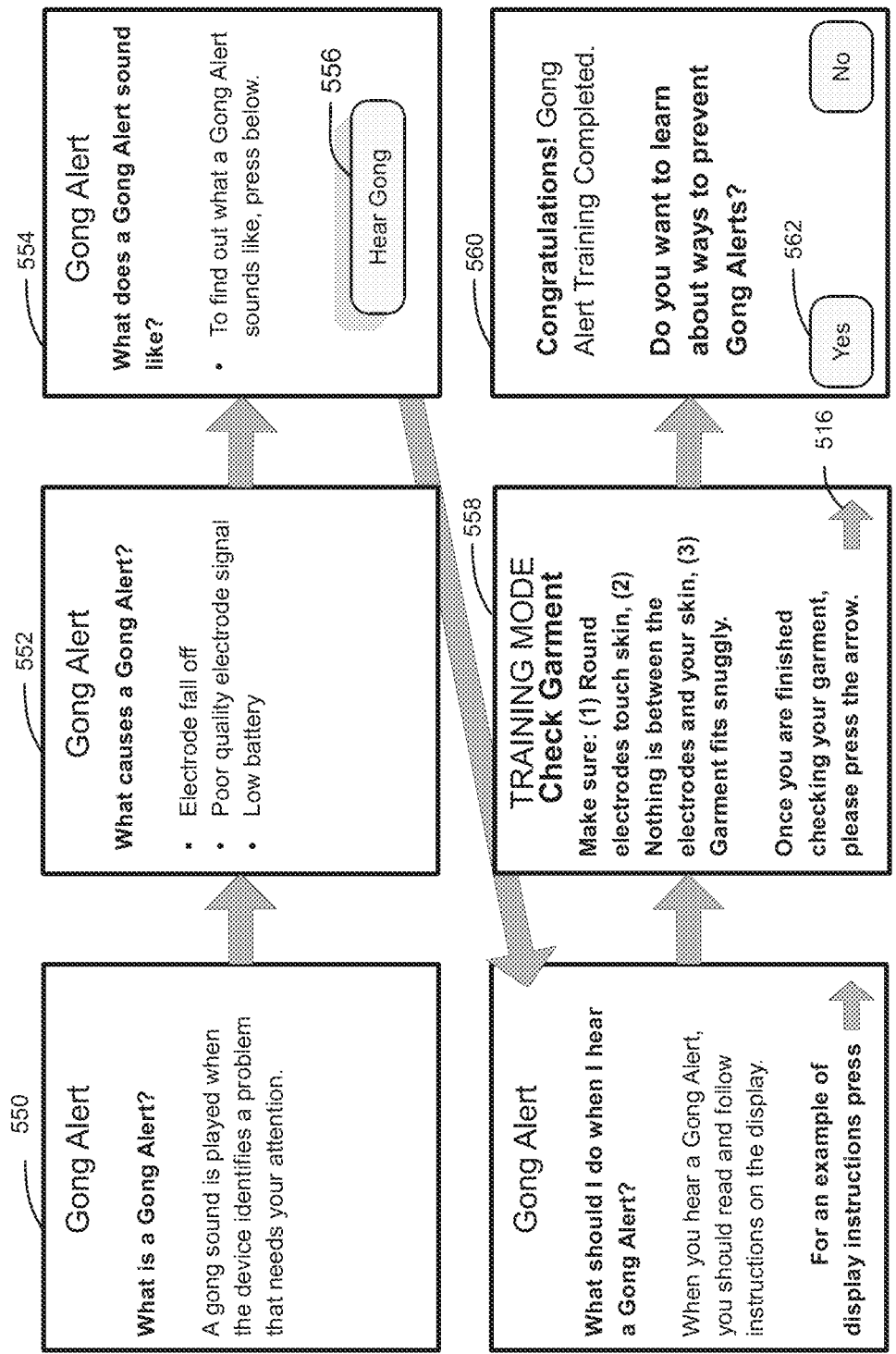
FIG. 6 is another example set of screens for selecting and accessing a training module on an external medical device.

Example Operational Sequences and User Interface:

With reference to FIGS. 5 and 6, exemplary screens or user interfaces that can be displayed to the user on, for example, the touch screen 212 (shown in FIGS. 2A, 2B, and 4) or other display are illustrated. The user interfaces can be controlled, for example, by the user interface manager 314 (shown in FIG. 3). The screens or user interfaces allow the user to perform numerous activities related to selecting and accessing training modules including, for example, reviewing a list of available training modules, selecting a training module of interest, viewing or accessing the training module, and selecting or scheduling a training module to view at another time. As previously discussed, the exemplary training modules described herein are intended to be viewed while the device is in the field and monitoring and/or determining whether to provide therapy to the user.

Further, it is appreciated that the screens and screen sequences described below are for illustration only and should not be construed as being the only way to implement the concepts described herein. For example, in the context of viewing a training module, the sequence of screens or the screens themselves can be changed from those shown in FIG. 5 to include other screen sequences or screens related to device and/or patient setup without departing from the spirit of the concepts described herein.

Selection of and Access to Individual Training Modules:

As shown in FIG. 5, the user can be provided with a main menu or home screen 510 including a menu of options or functions that the device can perform. One of the options, as shown by button 512, can be an option to access "Training". Selection of the button 512 causes the user interface to provide the user with an interactive list 514 of available training modules. Alternatively or in addition, the external medical device can include a dedicated training module button located on the device housing. Pressing the training module button can cause the screen to advance to the interactive list 514.

The interactive list 514 can include one or more training modules for the user to access or view. For example, one or more of the following training modules may be listed: "Treatment/siren alarm module", "After-treatment module", "Response button module", "Gong alert module", "Electrode falloff module", "Garment care and maintenance module", "Battery charge-level module", and "Charger module". The list of modules can be provided on a single screen or can be provided as a series or set of screens that the user can toggle or advance through, for example, by pressing a next or arrow button 516. The interactive list 514 can also include additional information that can assist a user in selecting a particular training module to access. For example, each listed training module can include an icon or indicator that shows one or more of the following: whether a user has previously viewed the module, whether a module has been specifically recommended for viewing by a caregiver or service representative, and/or an indicator of an importance or priority of a particular module. For example, if a training option has been previously viewed, or if the training module has been substantially completed, the training option may be grayed out or otherwise marked to indicate its status as being previously viewed. In some cases, the patient may be able to re-view a previously viewed or completed training module. In some examples, the available training modules can be listed in order of importance and/or can include a graphical representation of importance (e.g. red, indicating that the module should be viewed urgently; yellow, indicating that the module should be viewed at the next convenient time; or green, indicating that the module is optional and can be viewed if the subject matter is of particular interest to the user). The interactive list 514 can also include information about module duration, media type (e.g., slides, video, text, audio content) and/or a level of technical sophistication needed or recommended to appreciate the training module. In some examples, the additional information about the training module, which is not visible on the interactive list 514, can be shown in a popup box or notification, which can be accessed by selecting a particular training module. Similarly, in some other examples, as shown by screen 518, selecting a training module can provide a summary or bibliographic information screen with information that can help the user to decide whether to view the training module.

After reviewing some or all of the available training module options, the user selects a specific training module to access. For example, in the case of a touch screen display, the user can simply touch the portion of the screen, identified a button 520, corresponding to the training module of interest. In other examples, the user may toggle through available options using arrows, buttons, keys, or other data entry features of the external medical device to record a selection. In other examples, a selection can be entered audibly, by speaking a portion of the name of the training module of interest. In that case, a microphone associated with the device can record the user's command and audio processing techniques can be used to record the correct selection.

Once a selection is entered, a screen including a portion of the training module, referred to herein as first or title screen 522, is provided on the visual display. The title screen 522 can be the first of a series or set of screens with information about the topic of interest. The display screens can include, for example, a combination of text, drawings, visual indicators, animation, and/or embedded videos with information about how the external device functions and/or how the user may use the external medical device. In some examples, the title screen 522 can include a question of interest to the user. Subsequent screens in the training module can include information and examples that answer the question.

In some examples, the set of screens progresses automatically, such as after a sufficient period of time for the user to read the text contained on the screen (e.g., after 30 seconds or one minute). In other examples, the user manually advances to a subsequent screen by, for example, tapping or swiping a touch screen display or pressing a button on the medical device. In other examples, the user can advance to the next screen by pressing a button on the screen, such as arrow 516.

As shown, for example, at screen 524, some of the user interface screens included in a training module can include messages or notifications that the user would receive during normal operation of the device. For example, as part of the training module related to patient treatment, a screen with the instruction "Press Response Button Now" could be displayed. Similarly, in a training module related to monitoring garment fit, a screen with the message "Check Garment" can be provided. For instance, such a screen may additionally instruct the patient to check that the garment is securely fitted and not too loose about the patient's torso. Such a screen may also instruct the patient to make sure that the round electrodes touch his or her skin and that nothing is between the electrodes and skin. To ensure that the user recognizes that such screens are part of the training module and not an actual alert or notification from the device, the screen could also include a message or indicator, such as text indicating that the device is in "TRAINING MODE" and that the alert is merely for instructional purposes.

In some examples, some of the screens of the training module can include interactive content such as surveys, quizzes, questions, or tests. A user can be required to correctly answer a number of questions about the information taught by the training module before advancing to the next screen. Alternatively or in addition, a user may be asked to practice performing a device action as a form of test or quiz. For example, in the case of a wearable defibrillator, the user can be asked to practice pressing the response buttons (e.g., button 210 in FIGS. 2A and 2B). The user "passes" the test if the device determines that the activity, such as pressing the response buttons, was performed correctly and in a timely fashion. Similarly, a portion of the training module can include listening to or watching a device audio or visual alert or alarm and identifying an appropriate response to the alert or alarm. For example, in a training module discussing differences between different alarm sounds, the device can output a sound and the user may be asked to identify the type of sound (e.g., gong, bell, siren, buzzer, etc.). A follow-up question could ask the user what is the correct response to the type of sound that was played. By way of illustration, in the case of a wearable defibrillator, a siren alarm may be provided if the device identifies a cardiac event and is preparing to provide therapy to the user. In that case, the correct response would be to press the response buttons to cancel or delay the therapy. The device may provide a second type of alarm, referred to in some examples as a gong alarm, if the device identifies a problem that the user should correct (e.g., the battery needs to be replaced or electrodes need to be repositioned). In response to a gong alarm, the user is instructed to follow instructions on the device screen.

At the completion of a particular training module, as shown by screen 526, the user can be provided with a screen informing him or her that the selected training module has been completed. The module completed screen 526 can, for example, inform the user that the specific module is complete and can inquire whether the user wishes to review any part of the training module. Alternatively or in addition, the module completed screen 526 can identify or suggest another related module that the user could access to provide additional information about the medical device and/or patient conditions treated by the device. For example, the module completed screen 526 for a training module including information about what happens when an abnormal arrhythmia is detected by a wearable defibrillator device and about how the wearable defibrillator provides treatment to the user, could ask the user whether he or she wants to view a second training module including information about what to do after a treatment is received from the device. For example, after treatment is provided by the device, the device may be configured to provide a training module instructing the patient how to contact an emergency care provider (e.g., by calling 911) and/or another caregiver.

With reference to FIG. 6, another exemplary set of screens for a training module is illustrated. The training module provides information about how the user should respond to an intermediate alert, referred to as a Gong Alert. As shown in FIG. 6, the training module begins with a description of what a gong alert is, as shown at 550, and what types of device events trigger gong alerts, as shown at 552. Subsequent screens include interactive content that allows the user to experience and practice responding to a gong alert. For example, as shown in screen 554, a button 556 is provided that, when pressed by the user, causes the device to emit a gong sound. In some examples, in addition to providing the gong sound, the device may vibrate, the display may flash, or provide some other visual or tactile stimulus. In this manner, the user can become familiar with what happens when a gong alert is triggered. After listing to, viewing, and/or feeling the gong alert, the user can be provided with an exemplary instruction screen including instructions for responding to the gong alert. For example, as shown at screen 558, if the gong alert was triggered because of an improper garment fit (or if one or more sensors disposed in the garment are unable to acquire signals), the screen can include instructions for checking the garment fit and/or for making sure that the round electrodes contact the skin and that nothing is between the electrodes and the skin.

In some examples, the screen 558 can include text instructions for performing these actions. Additionally, the screen 558 can include diagrams, animations, or videos showing how these steps are performed. For example, the animation can show how tightly the garment should fit to the patient and/or how the round electrodes should be positioned against the skin. Further, it is noted that the instructions can be included over several screens. In that case, the user can advance to a subsequent instruction screen by, for example, pressing the arrow 516. In some examples, the device can be configured to only advance to a subsequent screen after the instructions included on a current screen are followed. Sensors associated with the device can be used to confirm when an instruction has been followed. In some examples, the screen 558, or a series of subsequent screens, can also include text instructions explaining why the gong alert was triggered and, in some cases, suggestions for preventing occurrence of alerts in the future.

Similarly, following the training module on gong alerts, in the module completed screen 560, the user may be asked whether he or she would like to view another training module with information about ways to prevent or reduce the occurrence of gong alerts. If the user agrees to access the additional training module, the device can provide access to a training module either immediately or at a scheduled later time. In the case of a gong alert triggered because of poor garment fit or because of loss of signal from the ECG electrodes, the additional or follow-up training module could include instructions for washing the garment to improve garment elasticity. For a gong alert triggered because of a low battery charge, the additional or follow-up training module could include information about how to monitor the battery charge remaining and/or about the importance of having a second fully charged battery available. Similarly, the training module could include information about time required to fully charge the battery or other topics that would help the user to better manage battery charge levels. The training module could also include information about what the device does to preserve power once a low battery warning is received and/or about what device functions (e.g., non-critical functions) are disabled after a low battery warning. In some cases, the next training module for viewing is selected automatically by the device. In that case, the user only needs to press the yes button 562 to begin the second or follow-up training module. In other cases, the user can select a training module to view from a list of alternatives, such as from the interactive list 514 shown in FIG. 5.

In addition to allowing the user to select from the list of optional training modules using the user interface and menus described above, the device can be configured to provide access to required training modules. A required or mandatory module can be requested by a caregiver or service representative, or can be scheduled according to a predetermined schedule that is created before the user receives the device. An example of a required training module could be a follow-up training module scheduled after the user has had the device for a few weeks and which reviews information provided to the user during initial device set up. For example, a user generally receives introductory training when he or she first receives the device. The training can include verbal instructions from a service representative along with instructions or lessons viewed on the device. The follow-up introductory training can review topics covered during introductory training to reinforce topics presented during the initial training session. In other examples, a required or mandatory training module could be a newly released training module with information about updates to the device and/or changes to procedures for interacting with service representatives or reporting problems with the device.

Figure 7:
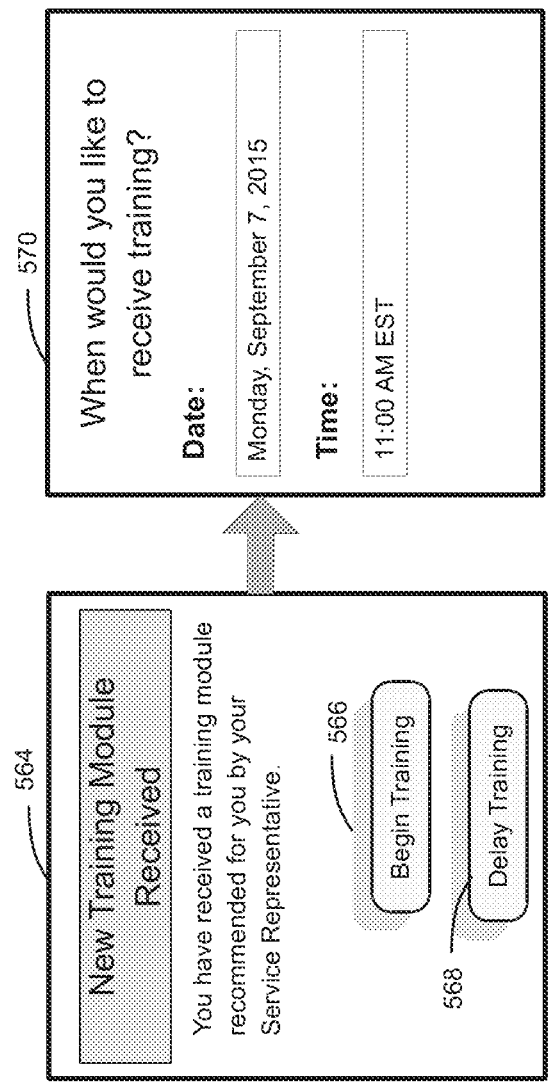
FIG. 7 is an example set of screens for scheduling when to access or view a training module on an external medical device.

With reference to FIG. 7, when a training module is received by the device, the user may be provided with a notification screen 564. For example, the training module may be a recommended or mandatory training module. The screen can explain that a recommended or mandatory training module is available and should be viewed at the earliest convenient time. The notification screen can include a "Begin" button 566 that gives the user the option to begin the training module immediately and/or a "Delay" button 568 that gives the user the ability to delay the module until a later time. If the user opts to delay the training module, a schedule screen 570 can be provided that allows the user to select a more convenient time for accessing and/or viewing the training module. In some examples, the device can be configured to monitor the number of times that the user delays the training module. If the training module is delayed more than a few times, the device can include a notification reminding the user of the importance of viewing training modules and/or can limit options for rescheduling (e.g., the training module must be rescheduled within the next few hours or can only be delayed for a period of time, such as one hour, but cannot be rescheduled to another day).

Integrated Device Fitting and Training Schemes:

In some examples, training modules can be integrated into a larger training scheme for particular patients and device types. A service representative or medical professional may initially introduce the training scheme to the patient by following a predetermined protocol during patient training and fitting. For example, a medical professional may follow an automated process in the field for initially fitting the patient with the medical device (e.g., a wearable cardiac device). The professional may be presented with an initial fitting checklist configured for the professional to complete with the patient before letting the patient leave with the device. Such a checklist can be presented in an interactive manner via one or more device user interfaces. The fitting checklist can be presented in the form of an animation, video, still images, text, etc. For instance, the fitting checklist can be configured to confirm if the professional has completed a task of the checklist: "Do you have all the garments for the patient?" or "Have you completed training the patient on how to adjust the vest appropriately?"

The professional and/or patient may be presented with a module that causes the device to step through a particular mnemonic phrase or acronym such as, for example, the acronym WEAR, which reminds users to (1) Wear the device all the time, except when showering, (2) to change the battery Every twenty-four hours, (3) to Act quickly for siren alarms, and to (4) Read the device display for gong alarms. The organization or order of the initial fitting and training session for the patient may substantially follow the acronym. For example, in the context of a wearable device, the module may direct the professional to input the patient's chest size and/or measurements and other related measurements (e.g., the corresponding garment size), when instructing the patient about the "W" portion of the acronym. In an implementation, the professional may need only input the patient's measurements, and the device can recommend an appropriate garment size for the patient based on the input patient measurements.

In some examples, the device can be configured to track the initial patient fitting process. Examples of items to track include but are not limited to: patient size (e.g., waist size, chest size, weight, etc.) garment size (e.g., small, medium, or large), belt size, electrode contact quality, and/or a quality of a signal received from patient sensors in the garment.

In some examples, each professional may be given access to the device through a unique user code. In this manner, all people who access the device can be tracked. Further, each professional may be asked to identify his or her reason for accessing the device. For example, such reasons may include fitting, setting change, follow up, device service, etc.

In some examples, the device can be configured to track time spent in each training module. The collected time data can be made available for analysis, e.g., on a user interface dashboard at a remote location for review. Similarly, the device can be configured to allow the professional to indicate topics or sections of initial device fitting and training that a patient had trouble understanding. Support services or automated follow-up through the principles described herein can be scheduled to address or review such topics. As previously noted, the fitting process can be overwhelming for patients. Accordingly, specifying areas of difficulty will allow for more efficient follow-up.

In some examples, the device can be configured to record audio and/or video during the fitting process for later analysis. Trainers or service representatives can review the recorded audio to identify points that professionals and patient representatives and/or patient struggle with so that those sequences can be updated/modified.

In some implementations, the device can be configured to allow for patient electronic signature on the device to confirm that he or she completed the initial training. For example, tools such as DocuSign for digital transition management can allow for patients to be able to electronically sign a patient agreement and, in some cases, a screen or display including the WEAR checklist.

In some examples, the device can be configured to automatically download the patient's settings once the device is configured for use with a particular patient. Additionally, the professional may key in a unique identifier associated with the patient, which is the provided to a remote server to cause the remote server to transmit, or the device to retrieve, the patient's unique device settings. Confirming patient identity and device settings can prevent human errors during initial device set up.

Figure 8:
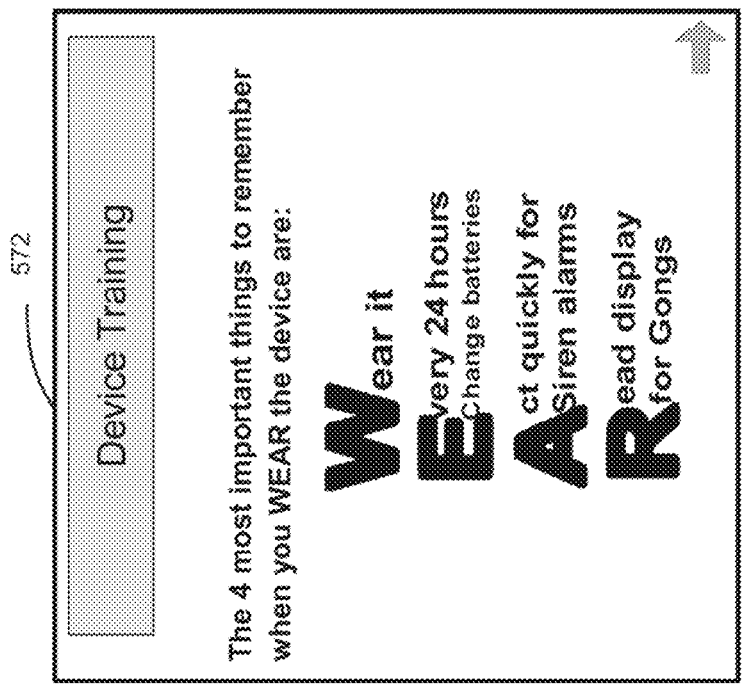
FIG. 8 is an example screen of a training module.

The patient-accessible training modules can be configured to reinforce one or more of the principles imparted during the initial training and fitting through the use of same or similar terminology and process as used during the initial patient fitting. For example, with reference to FIG. 8, in the case of a wearable defibrillator, training modules can all relate or refer to the WEAR acronym. The various training modules accessible to the user can be designed to reinforce the overarching mnemonic or acronym. For example, each training module can begin with a display 572 showing the WEAR acronym and reminding the user of the meaning of the acronym. A second or subsequent screen could show the user which aspect or portion of the acronym will be addressed by the particular training module being viewed. For example, when accessing a training module about monitoring battery charge and/or remembering to replace the battery at an appropriate time, the training module can highlight or direct the user's attention to the letter "E" in the acronym. In this way, the user is reminded of how the particular activity or training event being addressed relates to the larger scheme for operating and caring for the device. Similarly, training modules can be designed or organized with the acronym in mind, so that the user or patient receives information about device function in a manner related to or organized according to the acronym. For example, a first training module of a series of training modules can include information about wearing the device. Information related to other letters of the acronym can be covered in order by subsequent training modules.

Figure 9:
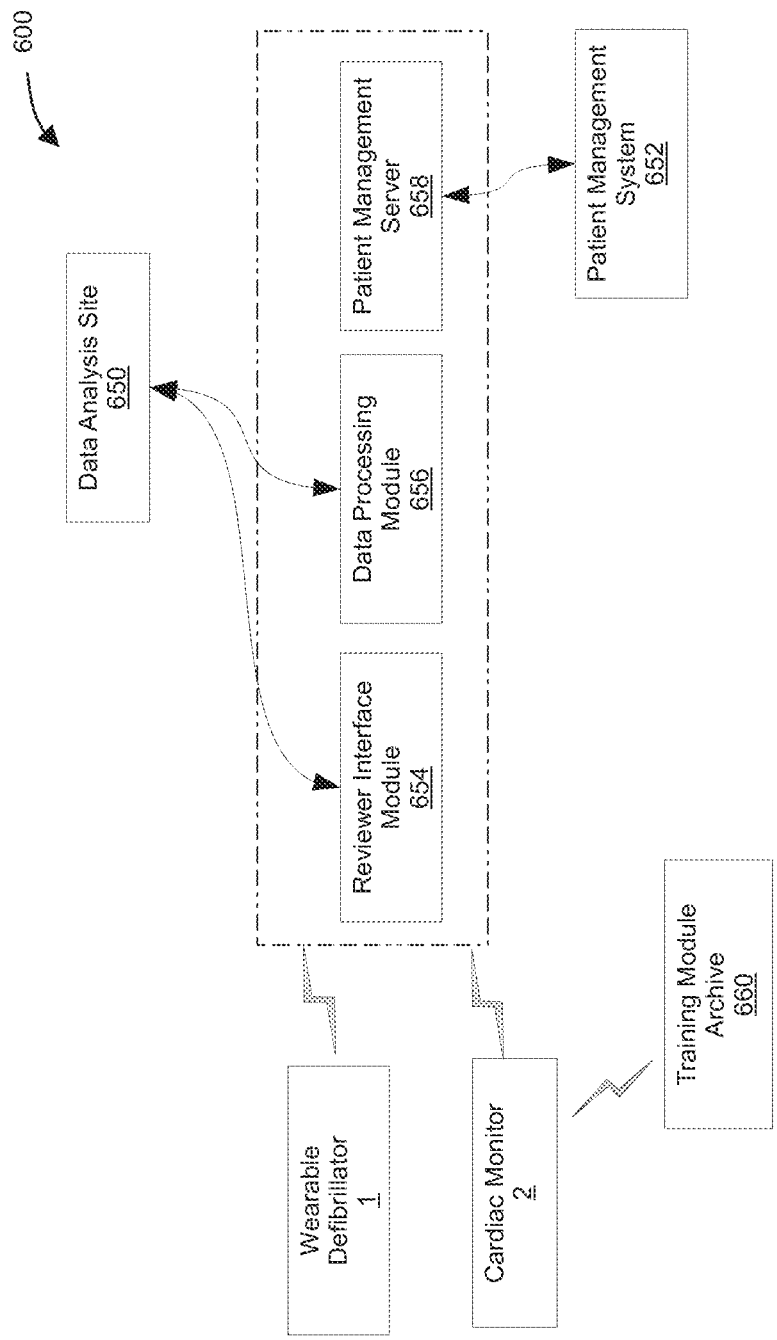
FIG. 9 is a schematic drawing of a communication system for an external medical device and cardiac monitor including a training module archive.

Communications Capabilities:

With reference to FIG. 9, a medical monitoring system including the external medical device in combination with other data processing and acquisition components (referred to in combination as a communications network 600) is illustrated. The medical device includes communications circuitry, such as the network interface 306 (shown in FIG. 3), for wirelessly communicating with the communications network 600. The communications network 600 can be used for sending physiological information from a therapeutic medical device (wearable defibrillator 1) and/or a monitoring medical device (cardiac monitoring device 2) to one or more remote locations for analysis and/or review. The communications network 600 can also be used to transmit information, such as selected or newly created training modules, from an external source to one of the mobile devices (defibrillator 1 and/or monitoring device 2).

Data Transmission:

In some examples, the communications network 600 includes multiple components or modules for receiving, analyzing, and providing cardiac data to an end-user, physician, or interested third party. For example, in some implementations, the communications network 600 includes a reviewer interface module 654, a data processing module 656, and a patient management server 658. The reviewer interface module 654 includes a combination of software and hardware that allows a live technician or reviewer to identify and/or to confirm any of a number of patient conditions based on review of recorded physiological data, such as ECG data. For example, events that can be identified or confirmed by the reviewer include one or more of the following: atrial fibrillation, bradycardia, tachycardia, atrioventricular block, Lown-Ganong-Levine syndrome, atrial flutter, sino-atrial node dysfunction, cerebral ischemia, syncope, atrial pause, and/or heart palpitations. In reviewing ECG data and/or device data, the technician or reviewer may recognize occurrences of events or device misuse that can be addressed or corrected by training. In that case, the reviewer or technician can suggest training modules including information that addresses the identified issues. As discussed in greater detail below, selected training modules can be wirelessly transmitted to the user's device via the communications network 600.

The data processing module 656 includes computing devices configured to automatically analyze physiological information and/or device use information recorded by the medical devices 1, 2 using algorithms that provide an indication of patient status and/or cardiac function. The patient management server 658 includes computing devices that compile or accumulate patient reports prepared based on analysis of patient physiological information in the reviewer interface module 654 and/or data processing module 656, and makes the patient reports available to interested parties such as the user, the user's family, caregivers, and/or a responsible or prescribing physician. Based on evaluation and analysis of device and physiological information, including ECG data, the data processing module 656 can also automatically identify training modules for a user. The training modules can be provided to the user's device in the manner discussed above.

With continued reference to FIG. 9, the communications network 600 can be configured for wired or wireless communication between the devices and modules. For example, the network can include wired connection elements, a long range wireless network (WiFi), a short-range wireless network (BLUETOOTH®), a cellular network, and/or combinations thereof for transmitting data from the medical devices 1, 2, and between the modules 654, 656, 658. Information (e.g., detection of a predetermined event, device use pattern, or request for a training module) can be sent from the medical device 1, 2 over the communications network 600 based on a request by the patient, automatically based on identification of an event on the device, and/or based on a request from a remote party such as a treating physician.

Training Module Acquisition:

In addition to transferring physiological information from the devices 1, 2 to the modules 654, 656 or data analysis site 650, the communications network 600 can also be used for transmitting information, such as training modules stored on the network 600, from a remote location to the devices 1, 2. In some examples, additional or newly created training modules can be stored on an external server, such as the patient management server 358, configured for wireless communication with the medical devices 1, 2. Alternatively, training modules can be stored on a separate server or storage module, such as the training module database archive 660, shown in FIG. 9.

In some examples, training modules can be sent to the wearable defibrillator 1 or monitoring device 2 from the patient management server 658 or the training module archive 660 over the communications network 600 automatically and without being requested by the device 1, 2 and/or patient. For example, the server 658 or archive 660 can send a new or updated training module periodically according to a predetermined schedule. Training modules can also be sent aperiodically. For example, an updated training module can be sent to the defibrillator 1 or monitoring device 2 as soon as it is ready for distribution and without waiting for a scheduled download time.

More specifically, in some examples, the training modules are automatically provided to the medical devices 1, 2 and stored on computer readable memory, such as the data storage 304 (shown in FIG. 3), on the medical device 1, 2 until the user is ready to access the training module. For example, the server 658 or archive 660 can be configured to accumulate a number of training modules and to automatically send the accumulated training modules to numerous of medical devices 1, 2 at one time in the form of a batch download. The batch download can be scheduled for a time when the device 1, 2 is unlikely to be performing other processing intensive tasks such as, for example, times during the day when the user is unlikely to be accessing the user interface and/or viewing other training modules. The batch downloads can be received by the medical device 1, 2 and the list of available training modules can be updated accordingly.

In some examples, the user can receive notifications, such as the notification screen 564 shown in FIG. 7, making him or her aware that new or updated training modules are available to access. If some of the new or updated modules are identified as being mandatory, the devices 1, 2 can notify the user and ask him or her to either view the mandatory training module immediately or to schedule the training module for later viewing. If the received training modules are categorized as being optional, the user can access the training module by viewing the interactive list 514 shown in FIG. 5.

In other examples, downloading new or additional training modules from the external server 658 or archive 660 to the medical device can be performed manually. For example, the user can view a list of training modules stored on the external server 658 or archive 660, and select modules of interest. The selected modules can be downloaded to the user's device 1, 2 via the communications circuitry. Alternatively, the user can select to stream training modules from the communications network 600 and/or server 658 rather than downloading them to the device 1, 2 prior to viewing. Allowing the user to view a larger library of available training modules than could be stored on the device 1, 2 itself, allows the user to select training modules that are more specifically tailored to his or her physical condition, level of interest, and/or amount of time available to view or access the training module.

In some examples, the user can select a training module that corresponds to his or her level of technical sophistication or which are more closely related to his or her particular physical condition. For example, patients with arthritis or who have difficulty manipulating smaller objects can select training modules with instructions tailored specifically for operating the device with certain physical constraints. Patients with good dexterity can be provided with training modules that ask them to perform more difficult tasks, such as tasks that require the user manipulate smaller buttons or multiple buttons at the same time. Similarly, the user can select training modules tailored for patients with certain vision or hearing abnormalities or deficiencies, if needed.

In other examples, a service representative can select new or additional training modules that could be downloaded to a particular patient. For example, through interactions with a particular user, a service representative could recognize that the patient is having trouble configuring the device, such as trouble connecting electrodes to the device controller. In response, the service representative could initiate the download of a training module, including information about how to configure the device and/or how to properly attach electrodes to the device monitor or controller. Once the training module is received, the user can receive a notification indicating that a module suggested by a service representative has been received and asking the user to begin the training module or to schedule a time for viewing the training module.

In other examples, a training module can be sent to the device 1, 2 in response to a request from the device 1, 2 and/or based on analysis of information received from the device 1, 2. For example, a patient can request a specific training module from the server 658 or archive 660. The request can be wirelessly sent from the device 1, 2 to the server 258 or archive over the communications network 600. The requested training module can be sent to the user's device 1, 2 by the communications network 600. Similarly, information representative of a patient event collected by the device 1, 2 can be sent to the server 658. In response to analysis of the received information, the server 658 can send a training module to the device 1, 2 for viewing by the patient. Similarly, the device 1, 2 can send a notification to the server 658 when a particular device use pattern is identified. The server 658 can send a training module to the device 1, 2 to address the identified use pattern. In other examples, the device 1, 2 can send a request to the server 658 or archive 660 to send any new or updated training modules at periodic or aperiodic intervals.

An example implementation for downloading training modules is as follows. A medical device can be configured to download data relating to one or more training modules from a server, e.g., on a periodic or aperiodic basis. For example, the medical device can be associated or paired with a wireless cellular communication device (such as base station 400 of FIG. 4) to facilitate the data download. In an implementation, the base station 400 can be configured to communicate with the medical device over a BLUETOOTH® connection. The base station 400 can be configured to receive connection requests from a remote server (e.g., a technical support service server). In an implementation, a support server application configured to execute on such a remote server can initiate a socket connection with the base station 400. Once the connection to the medical device via the base station 400 is established, the medical device can stream the data associated with one or more training modules. For example, the data can be a video stream that a patient can view live on a screen disposed on the medical device or base station 400. In some examples, the medical device can download an entire training module in a common format such as mp4. The training module can be displayed on the user interface of the medical device or base station 400, e.g., in a standard playback format with or without playback and other video controls such as HTML5. In an implementation, the downloaded training module data can be saved on a local memory of the medical device of the base station 400. In some implementations, the data can be discarded when the medical device battery is removed.

Scheduling Interface:

To organize scheduled training modules, the device can include a user interface and calendar for scheduling and/or reviewing when training modules are scheduled to begin. For example, as shown in FIG. 10A, the user interface can include a screen 574 with a list 576 of scheduled training modules. In addition to including a brief title or description of the scheduled training module, the list 576 can also include columns for a number of other relevant fields including, for example, the module name, a brief description of the subject matter of the training module, the scheduled date and time for viewing the training module, the date and time when the training module was released and/or received by the device, the individual (e.g., service representative, physician, caregiver, or user) who selected or scheduled the training module, and, in some cases, a priority or urgency indicator 578 describing a level of importance of the particular training module. For example, as shown in FIG. 10A, the priority indicator can be a number (e.g., 1=required; 2=suggested; 3=optional).

As discussed above, training modules can be scheduled manually (e.g., by the user or service representative) or can be scheduled automatically by the device based on measurements or information collected by sensors associated with the device. In other examples, the training modules can be prescheduled. For example, all users could be required to view a follow-up device setup training module at a predetermined period of time (e.g., 24, 48, or 72 hours) after receiving the device from a service representative.

In some examples, training modules can be automatically scheduled. For example, each time that the device receives a batch download of new or updated training modules, the device can automatically schedule the training modules for viewing at an available convenient time. The device can be configured to identify convenient times based on settings or preferences selected by the user or patient. For example, a user can select time periods during a day in which he or she is usually available to view training modules, such as when the user first wakes up in the morning, in the evening after eating dinner, or before the user goes to bed. In that case, the device can be configured to identify an available period of time within the selected window and automatically schedule a time for the user to view the training module. As discussed above, the user can delay or reschedule training modules if the time automatically selected by the device is inconvenient.

In other examples, training modules can be scheduled to view or review on a periodic basis. For example, a user may be required to view a training module with information about important device features, such as charging the battery or cleaning portions of the device on a periodic basis to reinforce topics covered during the patient's initial training. For example, a setup or general information training module could be scheduled for viewing periodically, such as every two or three weeks. In addition, various review or follow-up training modules for more specific topics could be scheduled throughout the year, giving the user the opportunity to review different device operating instructions on a regular basis.

In some examples, the training module list 576 is organized chronologically, in an order in which the training modules are scheduled. Similarly, the list 576 could be provided as an interactive calendar organized by day, week, or month. In other examples, the list could be organized according to other criteria such as: in order of importance or priority, based on who selected or scheduled the device, media type (e.g., video, audio, or text), and/or according to training module topic or subject matter. Further, in some examples, the list 576 can be provided as a popup notification that appears on another user interface screen, such as the home or main menu screens shown in FIG. 5.

Figure 10B:
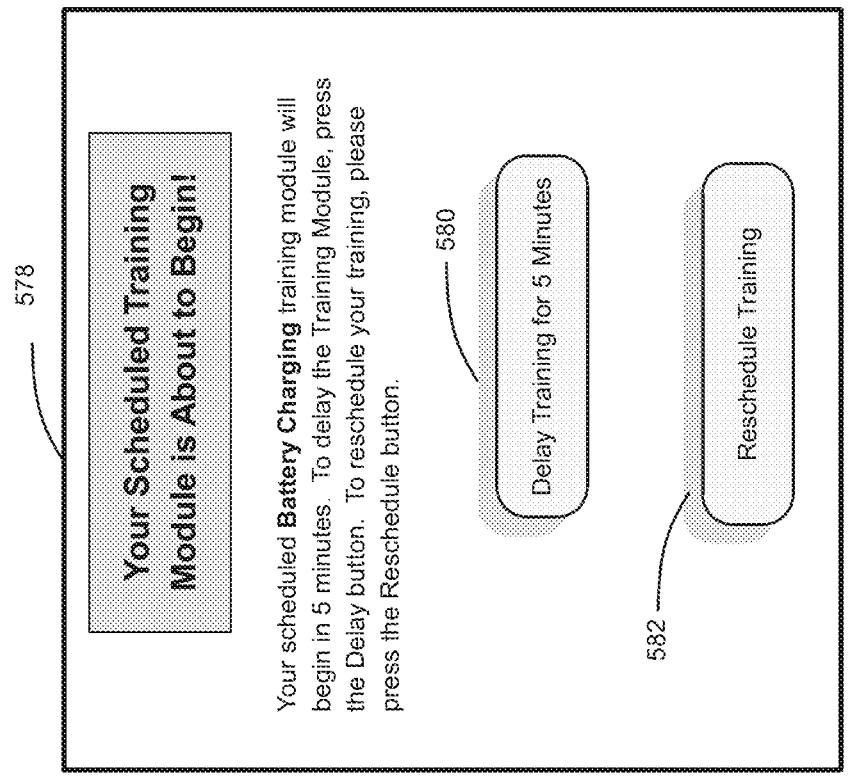

In some examples, as shown in FIG. 10B, the schedule interface can also include a notification feature. For example, the user can receive a notification 578 and a predetermined period of time (e.g., 5 or 10 minutes) before a training module is scheduled. The notification screen or feature can include a delay button 580 that allows the user to delay the training module for a short period of time (e.g., remind again in 5 minutes). The notification screen can also include a reschedule button 582 that allows the user to schedule a new date and time to access the training module. In that case, the training module can be rescheduled, and will appear on the list 576 at the rescheduled date and time. If the user selects the Reschedule Button 582, the device can provide a rescheduling page 584, as shown in FIG. 10C, that allows the user to select a new date and time to view the training module.

In some examples, the device can be capable of monitoring or recording a number of times that a training module is delayed or rescheduled. If a training module has been rescheduled multiple times, the device can be configured to provide more frequent or conspicuous notifications about the importance of accessing the training module. For example, if a training module has been delayed multiple times, a notification asking the user whether he or she would like to begin the training module could remain on the device home screen or main menu screen until the training module is completed. Similarly, if a user has delayed a particular training module multiple times, the device can automatically reschedule the training module for a new time rather than giving the user the option to select a new date and time. In other examples, if a training module has been delayed or rescheduled multiple times, the device can be configured to provide a notification or message to the user reminding him or her of the importance of accessing required or mandatory training modules. Further, if a training module has been delayed multiple times, the device can automatically begin the training module without giving the user the option of delaying or rescheduling it to increase the likelihood that the user will access or view at least a portion of the training module.

Training Module Selection:

Having described systems and processing routines for training module acquisition and an exemplary scheduling interface, processing routines for manually or automatically selecting a training module will not be discussed in detail.

In some examples, the user, patient, or caregiver manually selects training modules for the user to access. The selection can be made directly on the device or from a remote location (e.g., for a service representative, physician, or another third party). For example, a user can use the user interface discussed above in connection with FIGS. 5 and 6 to select and access a particular training module. Once a training module is selected, as discussed above, the device can either begin the training module immediately or provide the user the option to schedule the training module for a future date and time. The scheduled training module can appear on a schedule list or display screen and, at an appropriate time, a reminder or notification to view the training module can appear.

In some examples, training modules are also selected or prescheduled for the user when he or she first receives the device. As discussed above, prescheduled modules could include training modules that review topics discussed with the user by the service representative when he or she first receives the device. Some training modules can also be reoccurring training modules that reinforce best practices for operating and caring for the device on a periodic basis.

The device can also be configured to automatically identify training modules that the user or patient would benefit from accessing or viewing. Generally, the automatic selection of a particular training module is based on information received from sensors located on or associated with the medical device. The sensors can be configured to identify certain events or device use patterns that could damage the device, injure the patient, and/or reduce the device's ability to monitor and, in some cases, provide therapy to the patient. For example, the sensed information could identify that the user attempts to operate the device in an incorrect manner, that the user is having trouble taking care of the device (e.g., forgetting to wash the garment or forgetting to replace or recharge device batteries in a timely manner), or that the user is misusing the device (e.g., dropping or damaging the device).

With reference again to FIG. 3, the medical device controller 320 includes the sensing electrodes 328 associated with a sensor interface 312 and configured to receive physiological signals, which are often representative of cardiac function of the user or patient. As discussed above, signals, such as ECG signals, received by the sensing electrode 328 are transmitted to the processor 318 through the sensor interface 312. In some examples, the sensor interface 312 can also include additional sensors, such as contact sensors 330, pressure sensors 332, accelerometers or motion sensors 334, and others, for sensing or monitoring a status of the device and/or controller 120. Generally, the additional sensors 330, 332, 334, monitor aspects of the device and do not receive physiological information from the user. The sensor interface 312 and/or processor 318 can be configured to receive information from the sensing electrodes 328 and additional sensors 330, 332, 334, and to flag or identify unusual or improper readings that can be indicative of an event (e.g., electrode fall off, low battery warning) and/or of device misuse. For example, information received from sensing electrodes 328 and additional sensors 330, 332, 334 can be used by the controller 120 to identify when a portion of the medical device is incorrectly configured. In general, device configuration refers to the positioning of device elements (e.g., electrodes, garment, holster, controller, etc.)

on the patient and in the intended arrangement with relation to each other. Improper configurations could occur, for example, when ECG electrodes are incorrectly positioned on the patient's body, when portions of the garment are not correctly latched or locked in place, and/or when electrodes are not correctly connected to the controller or device monitor.

In some examples, the device or controller 120 can also include sensors 336 associated with the garment or electrode belt worn around the patient's waist. These sensors can be used to monitor compliance with device wearing and use requirements. In some examples, the sensors 336 can be associated with a buckle or clasp of the belt. In that case, the sensors 336 can be configured to identify when the buckle either is not latched or is latched incorrectly (e.g., buckle components are inserted together but not locked). In other examples, the device or controller 120 can include sensors associated with the port, such as port 202 shown in FIGS. 2A and 2B, which connects the ECG sensing electrodes 328 to the controller 120. More specifically, it has been found that some users will attempt to insert an electrode connector extending from the sensing electrodes 328 into the port 202 in an incorrect orientation (e.g., either backwards or upside down). If the sensors 336 associated with the port identify that the user has attempted to insert the connector into the port 202 in an incorrect orientation, the controller 120 can provide access to or schedule an appropriate training module with information about how to correctly connect elements of the medical device together.

If an improper use of the device or an improper configuration is identified, the device and/or an external source can select a training module with information to assist the user in correcting the improper configuration and/or for using the device in a safer or more effective manner. As previously discussed, if the selected training module is available on the device (e.g., is stored in data storage 304) the relevant training module can be provided to the user immediately. If the training module is not stored on the device, then it can be downloaded from an external source. If the user does not want to view the training module immediately, he or she can schedule a convenient time to view the selected training module.

In some examples, the device or controller 120 can also include sensors, such as battery charge sensors 338 or battery life sensors 340, associated with the battery 310 or power source of the device. The battery sensors 338, 340 can be configured to monitor battery charge and/or battery viable life and to provide an appropriate warning to the user when a battery charge is low and/or when a battery is nearing the end of its viable life. In some examples, the battery sensors 338, 340 can be associated with the user interface 308. The user interface can include a battery charge indicia, such as a gauge icon illustrating the percentage of battery charge remaining. Alternatively, a numerical score, such as an estimated number of hours or days until the battery will need to be recharged or replaced can be provided to the user. The user may be instructed to recharge or replace the battery before the charge reaches a predetermined threshold level.

The user interface 308 can also be configured to provide a notification or alert if the battery charge level drops below the threshold level. Further, if the device detects that the user consistently allows the battery charge to drop below the threshold level, the device can provide training modules with information about monitoring battery level to improve user compliance.

Having generally described a medical device and controller 120 configured to automatically select a training module for a user or patient based on information from the sensing electrodes 328 and additional sensors 330, 332, 334, specific examples of types of information that can be received and training modules that can be selected in response will now be discussed in detail. It is noted that the medical device or controller 120 need not necessarily include sensors for measuring each of the predetermined events or use patterns described below. Further, it is understood that other types of sensors than those expressly listed in these examples could be used to determine or identify types of events and/or use patterns found to be particular problematic for certain users. It is also noted that, in some examples, other training modules including additional and/or alternative information could be provided to the user in response to the predetermined events or use conditions described herein. Accordingly, the types of identified events and use patterns and training modules provided in response thereto are not intended to be a limiting or an exhaustive list of types of events that could be identified by sensors associated with the medical device and/or of the types of information that could be provided to a user through a training module.

Figure 11A:
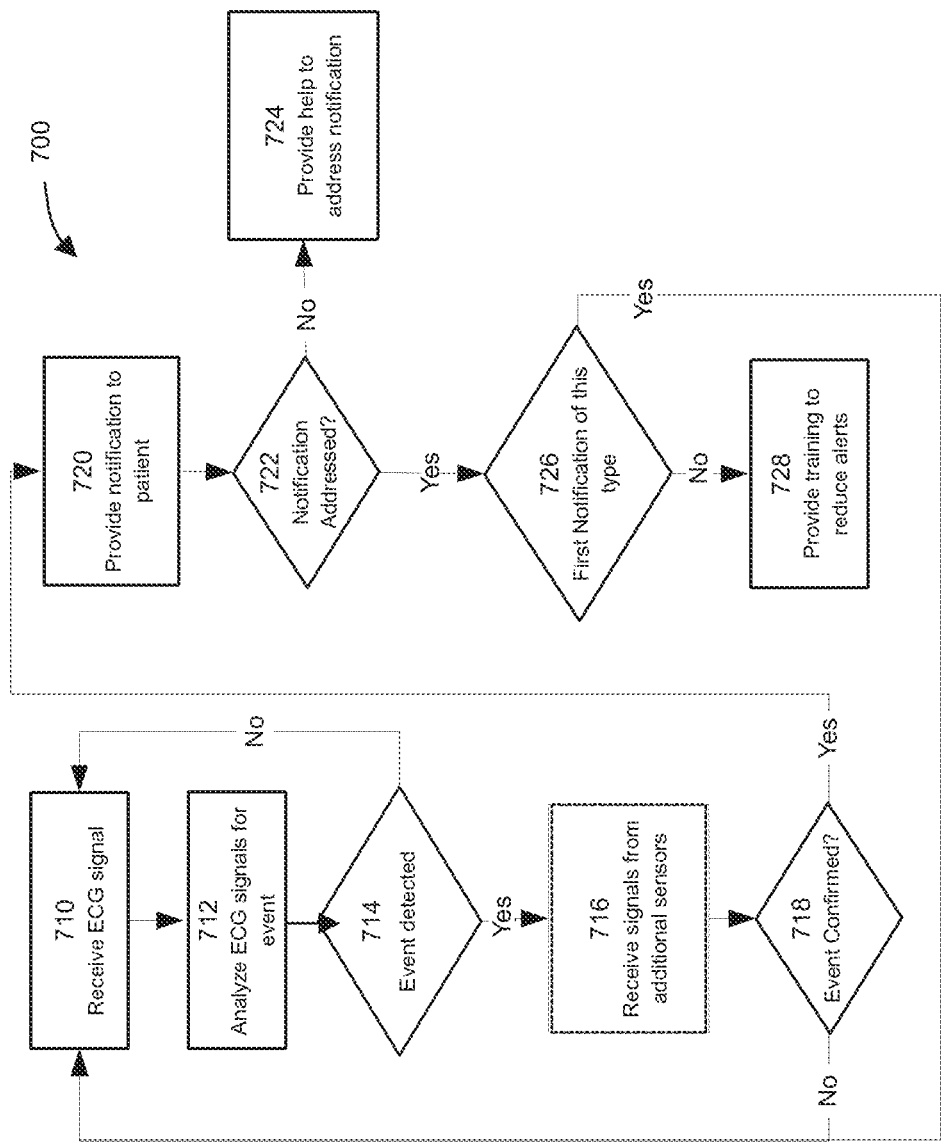
FIGS. 11A-11C are flow charts of exemplary processes for selecting a training module based on information received from sensors on or associated with an external medical device.

Electrode Placement and Electrode Fall Off Detection:

With reference to FIG. 11A, in one exemplary training module selection routine 700, as shown in box 710, an ECG signal can be received from ECG electrodes positioned on the user. For example, the signal can be automatically received by a processor located on or associated with the controller or monitoring device. Alternatively, the ECG signal could be received and processed at an external location remote from the monitoring device, such as a patient data server. As shown in boxes 712, 714 the received signals are analyzed to determine whether the signals are representative of an expected or substantially normal patient ECG (e.g., the received signal has the correct magnitude, direction, and shape). If the received ECG signal is substantially correct, it is likely that the ECG electrodes are correctly positioned and that none of the electrodes have fallen off. In that case, the device can continue to analyze the received ECG signal either continually or at predetermined intervals. However, if the received ECG signal appears to be unexpectedly weak or otherwise incorrect, then it is possible that there is a problem with the configuration of the electrodes.

In some examples, an electrode fall-off signal having a predetermined frequency can be applied to the patient's body and sensed via the ECG sensors. For instance, the ECG sensing interface can incorporate a falloff detection circuit. The circuit causes a low level AC signal (e.g., 500-1000 Hz signal) to be applied to the patient's body and sensed by each ECG electrode circuit. The signal may be a digitized stream, e.g., digitized at 1 Hz intervals, to allow for continuous or substantially continuous assessment of the electrode fall-off status.

Optionally, as shown at box 716, signals can be received from additional sensors, such as non-physiological sensors associated with the ECG electrodes, which are not involved in receiving the ECG signals. The additional sensor information can be used to provide confirmation and/or an additional indication about the configuration, contact, or position of the electrodes. For example, the additional sensors can be contact or proximity sensors, such as contact sensors 330 shown in FIG. 3, configured to identify whether the ECG electrodes are properly in contact or in proximity with the patient's skin and with sufficient adhesive force to obtain a good ECG signal. Similarly, in some examples, for a wearable medical device, such as a wearable defibrillator, the contact or proximity sensors can be associated with the garment and positioned to ensure that the garment and ECG electrodes attached thereto are correctly positioned and that the garment is tight enough against the user's body that good contact between the ECG electrodes and patient is obtained. In some examples, the additional sensors can include or be associated with positioning sensors that are configured to identify the position of the ECG electrode relative to the patient's body to confirm whether the ECG electrodes are correctly positioned to record an ECG signal.

As shown in box 718, signals received from the ECG electrodes and additional sensors are evaluated to assess whether the ECG electrode signals and other information confirm that an event has occurred. For example, information from the ECG electrodes and additional sensors could be used to evaluate the contact and positioning of the ECG electrodes. If it is confirmed that the electrodes have fallen off or are positioned incorrectly, the controller or device can issue a flag or alert indicating that the user may reposition the electrodes, as shown at box 720. If further analysis of the ECG signal and/or information from the additional sensors does not indicate that an electrode has fallen off or is positioned incorrectly, then the device can continue to monitor the measured ECG in the manner discussed above.

As shown at box 722, if the user successfully corrects the identified problem, then the alert can be deactivated and the device can continue to monitor ECG quality and/or ECG electrode placement in the manner discussed above. However, if the alert is not addressed within a suitable period of time, as shown at box 724, the device can suggest that the user view a training module related to electrode placement and/or garment care. The training module can be viewed immediately or can be scheduled for the user to access or view at a later time.

In addition, as shown at box 726, the device can determine whether the notification or alert was the first notification of a particular type. If the device identifies that multiple similar notifications have been provided to the user, as shown at box 728, the device can suggest a training module with information that will help the user to reduce the number of alerts. The training module can be suggested even if the user properly responds to a particular alert or flag. For example, the suggested training module can include information about how to reduce the occurrence of alerts and/or about proper use of the device so that alerts do not occur.

The information obtained from the ECG sensing electrodes and additional electrodes can also be used to verify user compliance with instructions for wearing the device. The user can be provided with instructions about when to wear the medical device and, in some cases, activities to perform while wearing the device. For example, the user can be instructed to wear the device for a predetermined duration each day and/or at specific times of the day or week. In other cases, the user may be instructed to perform one or more guided activities (e.g., a patient walk test) when wearing the device. Signals received from the ECG sensing electrodes and/or additional sensors can be used to verify if the user complies with the instructions. For example, if no ECG signal is received during a particular period of time when the user was instructed to wear the device, it is likely that the user is failing to comply with the instructions. Similarly, if the user's ECG signal indicates that he or she is resting at a time when a walk test is supposed to be performed, then it is likely that the user has failed to follow the instructions to begin the walk test. If the device identifies that the user is failing to comply with instructions, then training modules can be selected with information about how to respond to device notifications and about the importance of complying with instructions from the device.

Figure 11B:
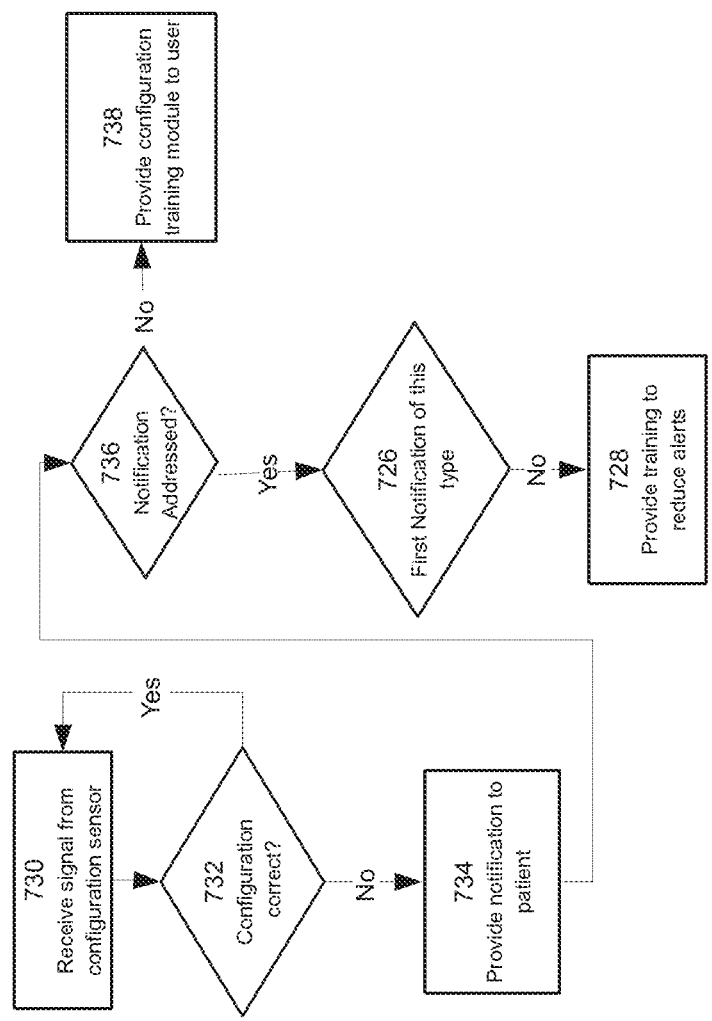

Garment Fit and Device Configuration Detection:

With reference to FIG. 11B, in some examples, signals from the additional sensors can be used to identify device configuration and whether the user is wearing the device correctly. For example, as shown at box 730, a signal can be received from an additional sensor associated with a wearable portion of the device (e.g., a garment or device holster). Similarly, signals can be received from sensors associated with the device and configured to determine device components are correctly connected together. In combination, these additional sensors (referred to hereinafter in combination as "configuration sensors") can be used to identify whether the user has correctly configured the device.

As shown at box 732, the signals received from the additional sensors are analyzed to determine whether the device is configured correctly, and whether wearable portions of the device are fitted correctly to the patient. If the analyzed signals indicate that the device is correctly configured, then the device can continue to monitor configuration status using signals received from the sensors, but no corrective action is required. However, as shown at box 734, if an incorrect configuration is identified, then the device can output an alert or flag to the user.

As shown at boxes 736 and 738, if the user fails to appropriately respond to the alert within a suitable amount of time, then a training module can be provided to the user. The training module can begin immediately or can be scheduled for a later time. In some examples, the training module can include information, animations, or videos showing how to put on and take off the garment and belt. The training module could also include information about how to insert the monitor or controller in a holster or other carrying case. Further still, the training module can include instructions for tightening the garment and belt to achieve a better fit. Additionally, since washing the garment can shrink the garment to achieve a better fit, the training module can include information about how often the garment should be washed and instructions for doing so. The training modules can be presented together as a single training session or, as discussed above, can be provided sequentially. In that case, at the end of each training module, the user can be presented with an option for viewing another training module related to similar or related subject matter.

In addition, as discussed in connection with FIG. 11A, the device can monitor whether the user has previously received a particular type of notification at box 726. If the notification has been received previously, the device can provide a training module at box 728 to reduce the occurrence of alerts and alarms, even if the user responded correctly to the particular notification.

Figure 11C:
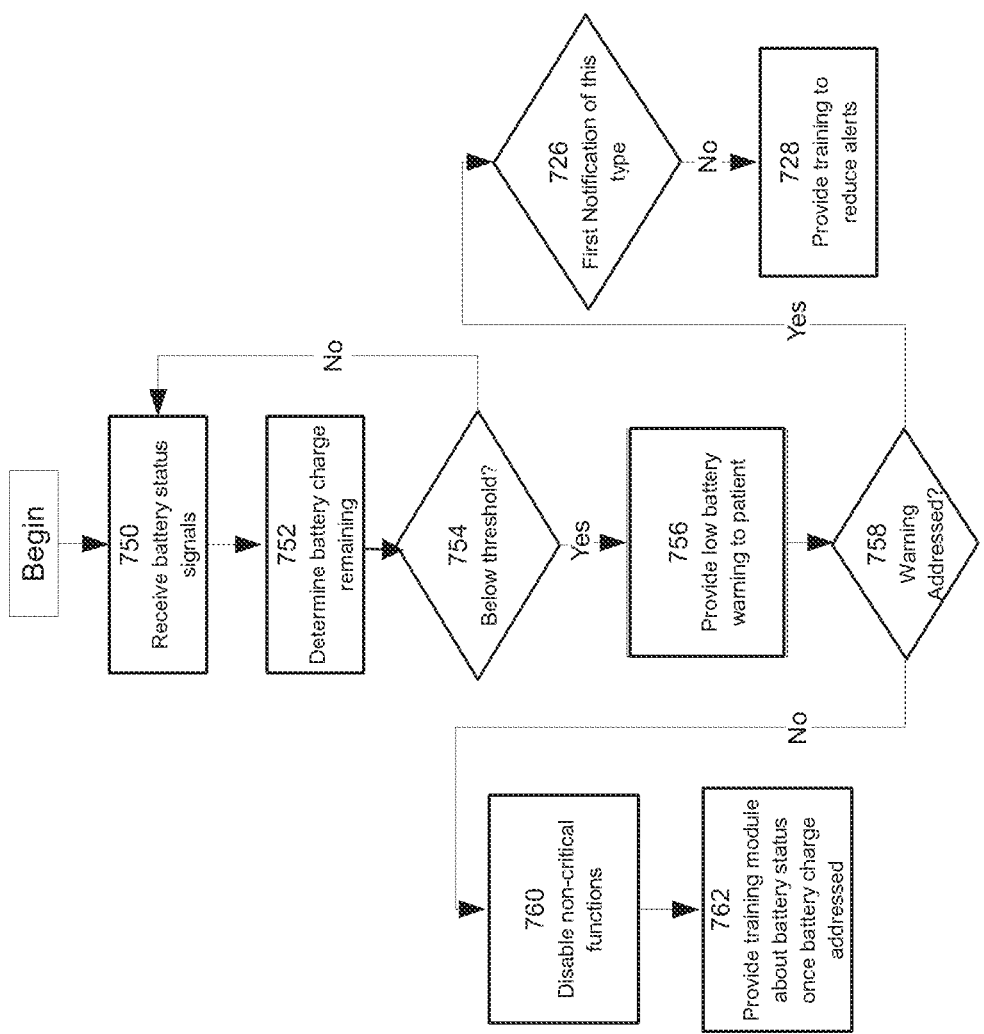

Battery Management and Charging:

With reference to FIG. 11C, the device can be configured to receive a battery status signal from the sensors associated with the battery as shown at box 750. For example, battery status signals can be received from battery sensors 338, 340 shown in FIG. 3. As shown at box 752, the battery status signal can be analyzed to determine a remaining charge of the battery and/or whether the battery is nearing an end of its viable life. As discussed above, in some examples, the charge remaining or viable life can be displayed on the device, such as in the form of a battery gauge. If the analysis determines that the remaining charge or viable life falls below a predetermined threshold level at box 754, the device can provide an alert or flag as shown at box 756.

As in previously described examples, the device monitors whether the user responds to the alert or flag in an appropriate manner as shown at box 758. For example, in the case of a device having a replaceable battery, a correct response could be to remove the exhausted or nearly exhausted battery and replace it with a fully charged battery. As discussed above, the fully charged battery could be located in a base unit or some other auxiliary charging device. If the replacement battery is determined to have a suitable charge and viable life, the device can continue monitoring the battery status signal as discussed above. In other examples, the user can respond to a low battery warning by connecting the device and/or controller to a power source for charging.

If the battery warning is addressed within a suitable period of time, the device may take no further action related to user training. However, the device can be configured to monitor the number of times that a particular type of notification, such as a low battery warning, is received, as shown at box 726. If it is determined that the user has received numerous low battery warnings within a short period of time, as shown at box 728, the device can provide a training module with instructions for how to monitor battery charge level and battery status. The training module is provided for the purpose of improving user compliance and reducing the number of alerts provided by the device.

In some implementations, the training module may provide information regarding the frequent warnings received by the user. For instance, the frequent warnings may be an indication of an underlying device issue. As such, the user may be informed that he or she can contact technical support for assistance.

As shown at box 760, if the user fails to respond to the alert in a timely manner, the device can begin to disable non-critical functions. For example, in response to the low battery warning, the device can turn off or suppress access to training modules, as well as training module acquisition and notification functions. Other non-critical features of the device, including visual displays, audio alerts, and wireless connectivity, can also be disabled to preserve remaining battery life.

Once the low battery warning is addressed and battery function stored, as shown at box 762, the device can provide access to a training module with instructions for monitoring and caring for the device battery. As previously noted, in various implementations, the device may continue to monitor and protect the patient during the administration of one or more training modules. Accordingly, in such examples, the training module may be configured to demonstrate device use and features through a mode that discourages the patient from performing the actions described in the training module. For instance, in a training module involving replacing the battery and monitoring battery charge or viable life, the patient may be presented with a video or animation showing proper steps and/or actions to be taken. The device may also be configured to notify the patient that the training is only to be viewed and the actions portrayed may not be followed during the training module. The training module may, for example, be configured to instruct the patient on battery maintenance issues by displaying information regarding how to periodically view a battery gauge on the device screen, and replace or charge the device before the low battery warning issues. Additionally, the training module could be provided to the user with information about the importance of monitoring battery charge and of charging or replacing the battery well before the battery reaches a lower power or critical status. The training module could also include an explanation of why certain features are disabled when battery power reaches a low stage and could remind the user of the importance of having these features available at all time.

Alarm Response:

In other examples, the device can be configured to monitor device use patterns such as, for example, the user or patient's response to particular alarms. As discussed above, the device can be configured to include various alarm levels or intensities (e.g., gong alarms and siren alarms). The user can be instructed to respond to different alarms in different ways. For example, the user can be instructed to immediately press a response button to delay or cancel treatment when the device emits a siren alarm. In contrast, the user or patient can be instructed to read and follow on screen instructions when the device emits the lower intensity gong alarm. If the user responds to a gong alarm by pressing the response buttons and/or to a siren alarm by pressing the display touch screen rather than the response buttons, the device can record or flag such actions as instances of incorrect use of the device. If multiple instances of incorrect use of the device are identified, the device could determine that the user or patient may access a training module with instructions for differentiating between different types of alarms and for how to respond to the different alarm types. In some examples, a user's response to or improper response to a siren alarm and/or when the device provides treatment to the wearer may be a predetermined event which causes the device to display a training module. For example, in response to the predetermined event (e.g., the wearer's failure to respond to a siren alarm), a training module may be provided instructing the wearer in appropriate post-treatment actions. For example, appropriate post-treatment actions may include calling 911 and/or informing a caregiver or another responsible person that the wearable device provided treatment. The training module may include information about, for example, which situations require the wearer to contact emergency personnel directly and which, less urgent situations, require notifying the caregiver or another responsible person.

Identifying Device Misuse and Drop Detection:

In some examples, the device can include sensors configured to identify device misuse rather than merely monitoring instances in which the user or patient fails to perform an expected task. For example, sensors associated with the device housing can be configured to identify when the device is dropped or when the device is subjected to a substantial and unexpected force (e.g., if a user hits the device or drops a heavy object on the device). If the device detects a device abuse event or indication (e.g., the device suffers an impact exceeding a threshold amount or device accelerometers indicate vibration in excess of a threshold amount) the device can automatically notify the user of the detected misuse event. For example, the device can include an Equipment Abuse Notification process as described in U.S. Pat. No. 8,676,313, entitled "Wearable medical treatment device with motion/position detection", which is hereby incorporated by reference in its entirety.

If numerous drops or unexpected mechanical or vibration forces are identified, the device can provide a training module that reminds the user about the sensitivity of device components and/or about the importance of ensuring that the device is correctly attached to the patient when the device is in use. Similarly, training modules with information about what to do if the user believes that the device has been damaged could also be provided. For example, a training module with information about how to contact a service representative to receive a replacement device and/or how to test the device to see whether the drop caused damage which would prevent the device from functioning normally could be provided.

Bathing, Showering, and Device Laundering Instructions:

In some examples, the device may detect an instance or a pattern of improper garment and device use and initiate patient training based on the detection. For example, to discourage a user from wetting the device (e.g., as detected by one or more water or humidity sensors), a training module instructing a user on how to remove the device prior to showering or bathing could be provided. Similarly, a training module related to device laundering could be provided. The laundering training module could include recommendations for types and amounts of soap or detergent and proper washer and dryer temperature settings (e.g., informing the user that the water temperature is not to exceed a predetermined temperature, such as 45° C., and/or to use a medium heat dryer). The training module can also include instructions to wash the garment alone and not with other clothing, to discourage the use of bleach, and to avoid letting the garment drip dry. In addition, the training module could include an explanation of how washing the device regularly improves elasticity of the garment, which improves garment fit and contact between the ECG electrodes and the user's skin.

Patient-Tailored Training Module Selection:

In some examples, the device can receive certain information about a particular user, which can be used to determine which training modules are well suited for the user. For example, during initial device set up, the service representative could manually enter information about the user. The entered information can be stored on the devices as patient profile data and/or patient data 316 shown in FIG. 3. The patient profile data can include, for example, a level of technical sophistication of the user, a level of medical knowledge or interest of the user, a degree of physical dexterity, as well as information about the user's eyesight and hearing abilities. Other exemplary patient information that can be used can include demographics information (age, gender, medical history, etc.), a language preference of the patient, data indicating the service representative assigned to the particular patient and device, the patient's primary care physician or other caregiver, and insurance data, among others.

Training modules can be selected based on the patient profile information. For example, a patient with substantial medical knowledge or an interest in medical topics may appreciate a training module that at least briefly explains why treatment is performed or provided. In contrast, a user with less medical knowledge or interest might only need to know what the device does prior to administering treatment without needing or appreciating a discussion of the underlying medical condition. Similarly, for patients with a high level of technical sophistication, training modules can assume that the user is able to perform general computer tasks such as selecting an option by pressing a touch screen. Similarly, it could be assumed that a technically sophisticated user does not require step-by-step instructions for adjusting device operating settings such as volume or display brightness and contrast. However, less sophisticated users may either need detailed instructions for performing these tasks or, in some cases, may need a service representative to assist in updating the device settings. In that case, the user could merely be instructed to contact the service representative if problems with the device are encountered.

The service representative can adjust these settings remotely or offer detailed instructions to the user explaining how the settings are adjusted.

In some examples, training modules can be marked according to a level of technical sophistication required (e.g., 1=easy/detail, 2=medium, 3=advanced). An easy or detailed training module can include substantial step-by-step guidance on how to operate or use the device. For example, the training module can include voice prompts and/or annotations for each step of the activity being taught. In some cases, the user will not be permitted to advance to a subsequent step or stage of the training module until he or she fully completes the tasks taught by the present step or screen. Such detailed training modules can take substantial time to complete and, due to the manner in which information is presented, could annoy more sophisticated users. An advanced module could include only a series of static screens and brief written instruction about the activity being performed. Further, for advanced training modules, the user may be able to read all screens before performing the activity rather than being required to perform each step in sequence before moving to the next stage taught by the training module.

In some examples, the device can be configured to assess information about the patient through a series of tests or activities. Information obtained from the tests or activities could be used to identify characteristics of the user, such as technical sophistication, interest in medical information, or understanding of previously explained instructions for operating and using the device. For example, a short quiz or test about how to use the device in certain situations can be provided to the user or patient a predetermined period of time (e.g., a few days or a few weeks) after he or she receives the device and initial training. The quiz or test could be provided as part of an additional or follow-up training module. If the user correctly answers the test questions, it can be assumed that the user has good recall of the instructions explained during initial device training. In that case, the device can be configured to provide advanced training modules to the patient and to skip training modules that cover simpler features of the device or which merely review topics covered during initial training. Alternatively, if the user or patient has difficulty recalling information discussed during the initial training session, the device can be configured to schedule a number of follow-up or review training sessions to provide the user or patient with the information about device operation for a second time.

Service Representative and Training Module Effectiveness Assessment:

As discussed above in connection with examples of processes for selecting training modules for the user, in some examples, the device can be configured to identify and record a number of alerts or flags related to events or use patterns of the device. For example, alerts or flags may issue when the quality of the signal from the ECG electrodes decreases, when the device is improperly configured, if a user responds to an alert in an incorrect manner, or if the battery charge or viable life is nearly exhausted (e.g., a low battery warning). In addition to automatically providing training modules for the user in response to the identified alerts or flags, the device can also be configured to notify a service representative that the user is experiencing problems with the device. The service representative can contact the user to discuss the alarms or flags. In addition, the service representative can recommend training modules and, if the recommended module is not already on the user's device, can send the module to the device via the communications network.

Additionally, patient device use and compliance data, such as the number of alerts and flags identified by the device, can be used to monitor and evaluate effectiveness of certain training modules and service representatives. For example, data representative of alerts or flags issued by devices that a service representative is responsible for can be obtained and accumulated by a central server or processor. For example, medical devices can be configured to transmit a notification to the controller or processor each time that an alert or flag is issued. Alternatively, each device can record or track the number of alerts issued and send a notification when the recorded number of alerts or flagged events exceeds a predetermined amount. The number of alerts or flags issued by each device can be tracked to identify trends (e.g., whether patient compliance is improving or worsening). The trends for users and/or devices for each service representative can be compared and evaluated to identify which service representatives are particularly successful in improving patient compliance.

In some examples, effectiveness of certain training modules can be tracked in a similar manner. For example, alert or flag notification frequency can be evaluated before and after a user views or accesses a training module to assess whether the training module improved user compliance and/or reduced the occurrence of alarms and flags.

The embodiments have been described with reference to various examples. Modifications and alterations will occur to others upon reading and understanding the foregoing examples. Accordingly, the foregoing examples are not to be construed as limiting the disclosure.

What is claimed is:

1. A wearable cardiac device comprising:
a computer readable memory;
a rechargeable battery;
a garment configured to be worn on a body of a patient;
one or more electrodes that are attached to the garment, that are configured to position against the body of the patient, and that are configured to detect a cardiac activity of the patient;
an audio and/or visual user interface comprising a display and/or a speaker for communicating training information to the patient; and
a controller that is powered by the rechargeable battery, the controller coupled to the computer readable memory and the audio and/or visual user interface, wherein the controller is configured to:
output, to the patient via the audio and/or visual user interface, a list of available training modules;
receive, from the patient via the audio and/or visual user interface, a user selection that identifies a first training module included in the list;
output the first training module to the patient via the audio and/or visual user interface, the first training module comprising instructions for laundering the garment, instructions for positioning the one or more electrodes with respect to the garment and the body of the patient, and/or instructions for charging the rechargeable battery;
record, in the computer readable memory, a plurality of alerts provided to the patient, the alerts indicating improper use of the wearable cardiac device by the patient;
detect a device use pattern indicative of the improper use of the wearable cardiac device by the patient based at least in part on the plurality of alerts;
automatically identify a second training module that instructs the patient as to a use or a configuration of the wearable cardiac device responsive to detecting the device use pattern; and
output the second training module to the patient via the audio and/or visual user interface.

2. The wearable cardiac device of claim 1, wherein the first training module further comprises instructions for device setup, instructions for responding to one or more of the plurality of alerts, and/or instructions for connecting the one or more electrodes to the controller.

3. The wearable cardiac device of claim 1, further comprising one or more sensors for detecting a status of the wearable cardiac device, wherein the controller is configured to detect the device use pattern indicative of the improper use of the wearable cardiac device based, at least in part, on measurements received from the one or more sensors and to inform the patient of the device use pattern indicative of the improper use via the audio and/or visual user interface.

4. The wearable cardiac device of claim 3, wherein the one or more sensors for detecting the status of the wearable cardiac device comprise an accelerometer, a temperature sensor, a gyroscope sensor, a drop detection sensor, a battery charge sensor, and/or a battery viable life sensor.

5. The wearable cardiac device of claim 1, further comprising one or more sensors for determining the configuration of the wearable cardiac device, wherein the improper use comprises an improper configuration, and the controller is configured to identify the improper configuration of the wearable cardiac device based, at least in part, on information received from the one or more sensors and to inform the patient of the improper configuration via the audio and/or visual user interface.

6. The wearable cardiac device of claim 1, further comprising a transceiver configured to receive (a) the first and second training modules or (b) an updated training module from an external source, wherein the controller is configured to provide a notification to a third party via the transceiver upon detection of the device use pattern indicative of the improper use of the wearable cardiac device.

7. The wearable cardiac device of claim 1, wherein the first and second training modules collectively comprise a video, an animation sequence, a plurality of still images, text messages, recorded messages, interactive content, quizzes, and/or surveys.

8. The wearable cardiac device of claim 1, wherein outputting the first training module to the patient comprises scheduling a time for the patient to use the first training module, informing the patient of the scheduled time via the audio and/or visual user interface, and, subsequently, providing notifications to the patient to remind the patient of the scheduled time.

9. The wearable cardiac device of claim 8, wherein at least one of the notifications includes an option for delaying the first training module to a later time.

10. The wearable cardiac device of claim 1, further comprising one or more sensors configured to measure information representative of: a respiration level of the patient, a heart sound and movement of the patient, a lung sound and movement of the patient, a tissue fluid level of the patient, a blood pressure of the patient, a glucose level of the patient, and/or a blood oxygenation level of the patient.

11. The wearable cardiac device of claim 1, further comprising a wearable defibrillator that comprises:
at least one therapy pad connected to or embedded in the garment and connected to a defibrillation shock generator; and
one or more sensors configured to monitor a status of the wearable defibrillator,
wherein the controller is operatively connected with the defibrillation shock generator and the one or more sensors, and
wherein the controller is configured to detect the device use pattern indicative of the improper use of the wearable cardiac device based, at least in part, on information from the one or more sensors.

12. The wearable cardiac device of claim 11, wherein the one or more sensors comprise a contact sensor to confirm contact between the one or more electrodes and the patient; a sensor associated with a latch or buckle of the garment to identify if the garment is secured to the patient; a sensor for confirming that the one or more electrodes are connected to the controller; a sensor for identifying a position of the one or more electrodes on the body of the patient; and/or a sensor associated with the at least one therapy pad to determine a position of the at least one therapy pad relative to the patient.

13. The wearable cardiac device of claim 1, wherein the improper use comprises device impact, dropping the device, water exposure, improper configuration, noncompliance with prescribed use, and/or noncompliance with recommended use.

14. The wearable cardiac device of claim 13, further comprising one or more sensors configured to monitor for the improper use, wherein the controller is configured to receive sensor readings from the one or more sensors indicative of the improper use.

15. The wearable cardiac device of claim 1, wherein:
the first training module further comprises instructions for device setup; and
the controller is further configured to output the first training module to the patient (a) prior to an initial wearing of the garment by the patient, and (b) between 24 and 72 hours after the initial wearing of the garment by the patient.

16. The wearable cardiac device of claim 1, wherein:
the first training module is a recurring training module that is scheduled for repeated use by the patient; and
the controller is further configured to output the first training module at predetermined intervals of wearing the garment.

17. A wearable cardiac device comprising:
a computer readable memory;
a rechargeable battery;
a garment configured to be worn on a body of a patient;
one or more electrodes that are attached to the garment, that are configured to position against the body of the patient, and that are configured to detect a cardiac activity of the patient;
an audio and/or visual user interface comprising a display and/or a speaker for communicating training information to the patient; and
a controller coupled to the computer readable memory, the audio and/or visual user interface, and the rechargeable battery, wherein the controller is configured to:
output, to the patient via the audio and/or visual user interface, a list of available training;
receive, from the patient via the audio and/or visual user interface, a user selection that identifies a first training included in the list; and
output the first training to the patient via the audio and/or visual user interface, the first training comprising instructions for laundering the garment, instructions for positioning the one or more electrodes with respect to the garment and the body of the patient, and/or instructions for charging the rechargeable battery.

18. The wearable cardiac device of claim 17, wherein outputting the first training to the patient comprises scheduling a time for the patient to use the first training, informing the patient of the scheduled time via the audio and/or visual user interface, and, subsequently, providing notifications to the patient to remind the patient of the scheduled time.

19. The wearable cardiac device of claim 17, wherein the controller is further configured to provide a notification to the patient to make the user selection to identify the first training via the audio and/or visual user interface.

20. The wearable cardiac device of claim 17, further comprising a transceiver configured to receive (a) the first training or (b) an updated training from an external source.

21. The wearable cardiac device of claim 17, further comprising a wearable defibrillator that comprises at least one therapy pad connected to or embedded in the garment.

22. The wearable cardiac device of claim 21, further comprising:
a defibrillation shock generator connected to the at least one therapy pad; and
one or more sensors configured to monitor a status of the wearable defibrillator,
wherein the controller is operatively connected with the defibrillation shock generator and the one or more sensors, and
wherein the controller is configured to detect a device use pattern indicative of an improper use of the wearable cardiac device based, at least in part, on information from the one or more sensors.

23. The wearable cardiac device of claim 17, further comprising one or more sensors for detecting a status of the wearable cardiac device, wherein the one or more sensors comprise an accelerometer, a temperature sensor, a gyroscope sensor, a drop detection sensor, a battery charge sensor, and/or a battery viable life sensor.

24. The wearable cardiac device of claim 17, wherein the first training comprises a video, an animation sequence, a plurality of still images, text messages, recorded messages, interactive content, quizzes, and/or surveys.

25. The wearable cardiac device of claim 17, wherein:
the first training is a recurring training module that is scheduled for repeated use by the patient; and
the controller is further configured to output the first training at predetermined intervals of wearing the garment.

* * * * *